US012618855B2

(12) United States Patent
Hardie et al.

(10) Patent No.: US 12,618,855 B2
(45) Date of Patent: May 5, 2026

(54) SERUM PROTEIN BIOMARKER PANEL FOR IDIOPATHIC PULMONARY FIBROSIS

(71) Applicants:Children's Hospital Medical Center, Cincinnati, OH (US); University of Michigan, Ann Arbor, MI (US)

(72) Inventors: William D. Hardie, Lebanon, OH (US); Assem Ziady, Newport, KY (US); Bethany Moore, Ann Arbor, MI (US)

(73) Assignees: Children's Hospital Medical Center, Cincinnati, OH (US); University of Michigan, Ann Arbor, MI (US)

( * ) Notice: Subject to any disclaimer, the term of this patent is extended or adjusted under 35 U.S.C. 154(b) by 983 days.

(21) Appl. No.: 17/766,556

(22) PCT Filed: Oct. 8, 2020

(86) PCT No.: PCT/US2020/054664
§ 371 (c)(1),
(2) Date: Apr. 5, 2022

(87) PCT Pub. No.: WO2021/072000
PCT Pub. Date: Apr. 15, 2021

(65) Prior Publication Data
US 2024/0103017 A1    Mar. 28, 2024

Related U.S. Application Data

(60) Provisional application No. 63/024,139, filed on May 13, 2020, provisional application No. 62/912,228, filed on Oct. 8, 2019.

(51) Int. Cl.
*G01N 33/68*    (2006.01)

(52) U.S. Cl.
CPC ..... *G01N 33/6893* (2013.01); *G01N 2800/12* (2013.01); *G01N 2800/52* (2013.01)

(58) Field of Classification Search
CPC ........... G01N 33/6893; G01N 2800/12; G01N 2800/52; A61P 11/00
See application file for complete search history.

(56) References Cited

U.S. PATENT DOCUMENTS 4,208,479 A    6/1980  Zuk et al.
7,741,038 B2    6/2010  Sarwal et al.
(Continued)

FOREIGN PATENT DOCUMENTS

AU        2013270447 A1    1/2014
WO    2009/038913 A2    3/2009
(Continued)

OTHER PUBLICATIONS

Zaman et al., Risk Factors for the Development of Idiopathic Pulmonary Fibrosis: a Review, Current Pulmonology Reports, pp. 118-125. (Year: 2018).*
(Continued)

*Primary Examiner* — Kathryn Elizabeth Limbaugh
(74) *Attorney, Agent, or Firm* — FBT Gibbons LLP; Nicole M. Tepe

(57)        ABSTRACT

The instant disclosure relates to methods for assessing pulmonary fibrosis disorder disease status in an individual in need thereof. One aspect of the disclosed methods may comprise: detecting a level of one or more biomarkers in a biological sample obtained from an individual, comparing the level of the one or more biomarkers to that of a control value corresponding to the one or more biomarkers, characterizing the disease status in the individual based on the level of the one or more biomarkers as compared to that of a relevant control value; and administering a treatment to
(Continued)

said individual based on the assessment of the one or more biomarker levels.

14 Claims, 2 Drawing Sheets

(56) References Cited

U.S. PATENT DOCUMENTS

| | | | |
|---|---|---|---|
| 8,017,577 | B2 | 9/2011 | Cooper et al. |
| 8,911,786 | B2 | 12/2014 | Desai et al. |
| 9,018,179 | B2 | 4/2015 | Kay et al. |
| 9,993,494 | B2 | 6/2018 | Appleman et al. |
| 10,126,295 | B2 | 11/2018 | Saavedra |
| 10,300,143 | B2 | 5/2019 | Sengupta et al. |
| 10,654,910 | B2 | 5/2020 | Spencer et al. |
| 10,761,099 | B2 | 9/2020 | Ziady et al. |
| 10,894,960 | B2 | 1/2021 | Ziady et al. |
| 2006/0142225 | A1 | 6/2006 | McSwiggen |
| 2006/0148828 | A1 | 7/2006 | Gianella-Borradori et al. |
| 2006/0153808 | A1 | 7/2006 | Cristofanilli et al. |
| 2006/0292562 | A1 | 12/2006 | Pollard et al. |
| 2008/0133141 | A1 | 6/2008 | Frost |
| 2012/0128782 | A1 | 5/2012 | Green et al. |
| 2013/0143752 | A1 | 6/2013 | Edmiston et al. |
| 2017/0042819 | A1 | 2/2017 | Goomer |
| 2017/0314074 | A1 | 11/2017 | Kossen et al. |
| 2017/0360749 | A1 | 12/2017 | Harijith et al. |
| 2018/0009873 | A1 | 1/2018 | Spencer et al. |
| 2019/0128901 | A1 | 5/2019 | Cozma |
| 2020/0341009 | A1 | 10/2020 | Ziady et al. |
| 2021/0102208 | A1 | 4/2021 | Ziady et al. |
| 2021/0302439 | A1 | 9/2021 | Ziady et al. |
| 2022/0202902 | A1 | 6/2022 | Ziady |
| 2023/0330121 | A1 | 10/2023 | Ziady et al. |
| 2023/0416782 | A1 | 12/2023 | Ziady et al. |
| 2024/0066021 | A1 | 2/2024 | Ziady et al. |

FOREIGN PATENT DOCUMENTS

| | | |
|---|---|---|
| WO | 2009/055671 A1 | 4/2009 |
| WO | 2011/038901 A1 | 4/2011 |
| WO | 2015/157546 A1 | 10/2015 |
| WO | 2018/208849 A1 | 11/2018 |
| WO | 2021/053058 A1 | 3/2021 |
| WO | 2022/031877 A1 | 2/2022 |

OTHER PUBLICATIONS

Cottin, V., "Lung biopsy in interstitial lung disease: balancing the risk of surgery and diagnostic uncertainty," Euro Respir J, 2016, 48(5):1274-1277, 4 pgs.
Hardie, W.D., et al., "Conditional expression of transforming growth factor-a in adult mouse lung causes pulmonary fibrosis," Am J Physiol Lung Cell Mol Physio, 2004, 286:L741-L749, 9 pgs.
Hardie, W.D., et al., "EGF receptor tyrosine kinase inhibitors diminish transforming growth factor-α-induced pulmonary fibrosis," Am J Physiol Lung Cell Mol Physiol, 2008, 294(6):L1217-L1225, 9 pgs.
Hardie, W.D., et al., "Emerging Concepts in the Pathogenesis of Lung Fibrosis," Am J Patho, 2009, 175(1):3-16, 14 pgs.
Hardie, W.D., et al., "Genomic Profile of Matrix and Vasculature Remodeling in TGF-α-Induced Pulmonary Fibrosis," Am J Respir Cell Mol Biol, 2007, 37(3):309-321, 13 pgs.
Hardie, W.D., et al., "Reversal of Lung Lesions in Transgenic Transforming Growth Factor α Mice by Expression of Mutant Epidermal Growth Factor Receptor," Am J Respir Cell Mol Biol, 1996, 15(4):499-508, 10 pgs.
Hutchinson, J., et al., "Global incidence and mortality of idiopathic pulmonary fibrosis: a systematic review," Euro Respir J, 2015, 46(3):795-806, 12 pgs.

Ikeda, Y., et al., "Iron Chelation by Deferoxamine Prevents Renal Interstitial Fibrosis in Mice with Unilateral Ureteral Obstruction," PloS One, 2014, 9(2):e89355, 10 pgs.
Korfei, M., et al., "Comparative Proteomic Analysis of Lung Tissue from Patients with Idiopathic Pulmonary Fibrosis (IPF) and Lung Transplant Donor Lungs," J Proteome Res, 2011, 10(5):2185-2205, 21 pgs.
Korfhagen, T.R., et al., "Rapamycin Prevents Transforming Growth Factor-α-Induced Pulmonary Fibrosis," Am J Respir Cell Mol Biol, 2009, 41(5):562-572, 11 pgs.
Kowdley, K. V., et al., "Serum Ferritin Is an Independent Predictor of Histologic Severity and Advanced Fibrosis in Patients With Nonalcoholic Fatty Liver Disease," Hepatology, 2012, 55(1):77-85, 9 pgs.
Krefft, S.D., et al., "Deployment-Related Lung Disorders," Federal Practitioner, 2015, 32(6):32-38, 7 pgs.
Lagares, D., et al., "ADAM10-mediated ephrin-B2 shedding promotes myofibroblast activation and organ fibrosis," Nat Med, 2017, 23(12):1405-1415, 29 pgs.
Le Cras, T.D., et al. "Inhibition of PI3K by PX-866 Prevents Transforming Growth Factor-α-Induced Pulmonary Fibrosis," Am J Pathol, 2010, 176(2):679-686, 8 pgs.
Ley, B., et al., "Epidemiology of idiopathic pulmonary fibrosis," Clin Epidemiol, 2013, 5:483-492, 10 pgs.
Lorusso, P.M., "Inhibition of the PI3K/AKT/mTOR Pathway in Solid Tumors," J Clin Oncol, 2016, 34(31):3803-3815,.
Lynch, D.A., et al., "High-resolution Computed Tomography in Idiopathic Pulmonary Fibrosis: Diagnosis and Prognosis," Am J Respir Crit Care Med, 2005, 172(4):488-493, 6 pgs.
Madala, S.K., et al., "Dual Targeting of MEK and PI3K Pathways Attenuates Established and Progressive Pulmonary Fibrosis," PLoS One, 2014, 9(1):e86536, 11 pgs.
Madala, S.K., et al., "Inhibition of the $\alpha_v\beta_6$ integrin leads to limited alteration of TGF-α-induced pulmonary fibrosis," Am J Physiol Lung Cell Mol Physiol, 2014, 306(8):L726-L735, 10 pgs.
Madala, S.K., et al., "MEK-ERK pathway Modulation Ameliorates Pulmonary Fibrosis Associated with Epidermal Growth Factor Receptor Activation," Am J Respir Cell Mol Biol, 2012, 46(3):380-388, 9 pgs.
Madala, S.K., et al., "p70 ribosomal S6 kinase regulates subpleural fibrosis following transforming growth factor-alpha expression in the lung," Am J Physiol Lung Cell Mol Physiol, 2016, 310(2):L175-L186, 12 pgs.
Magi, B. et al., "Bronchoalveolar lavage fluid protein composition in patients with sarcoidosis and idiopathic pulmonary fibrosis: A two-dimensional electrophoretic study," Electrophoresis, 2002, 23:3434-3444, 11 pgs.
Miller, B.W., et al., "FDA Approval: Idelalisib Monotherapy for the Treatment of Patients with Follicular Lymphoma and Small Lymphocytic Lymphoma," Clin Cancer Res, 2015, 21(7):1525-1529, 5 pgs.
Miller, M.R., et al., "Standardisation of spirometry," Euro Respir J, 2005, 26(2):319-338, 20 pgs.
Mimche, P.N., et al., "The receptor tyrosine kinase EphB2 promotes hepatic fibrosis in mice," Hepatology, 2015, 62(3):900-914, 23 pgs.
Nakashima, N., et al., "The p53-Mdm2 association in epithelial cells in idiopathic pulmonary fibrosis and non-specific interstitial pneumonia," J Clin Pathol, 2005, 58(6):583-589, 7 pgs.
O'Dwyer, D.N., et al., "The peripheral blood proteome signature of idiopathic pulmonary fibrosis is distinct from normal and is associated with novel immunological processes," Sci Rep, 2017, 7:46560 (12 pgs.) and Erratum: Sci Rep, 2017, 7:46860 (1 pg.), 13 pgs.
Peljto, A.L., et al., "Association Between the MUC5B Promoter Polymorphism and Survival in Patients With Idiopathic Pulmonary Fibrosis," JAMA, 2013, 309(21):2232-2239, 19 pgs.
Pellegrino, R., et al., "Interpretative strategies for lung function tests," Euro Respir J, 2005, 26(5):948-968, 21 pgs.
Richards, T.J., et al., "Peripheral Blood Proteins Predict Mortality in Idiopathic Pulmonary Fibrosis," Am J Respir Crit Care Med, 2012, 185(1):67-76.
Rops, A.L. W.M.M., et al., "Heparan sulfate proteoglycans in glomerular inflammation," Kidney International, 2004, 65(3):768-785, 18 pgs.

(56)　　　　　　References Cited

OTHER PUBLICATIONS

Seshacharyulu, P., et al., "Targeting the EGFR signaling pathway in cancer therapy," Expert Opin Ther Targets, 2012, 16(1):15-31, 25 pgs.

Shah, R., et al., "Circulating Extracellular Vesicles in Human Disease," N Engl J Med, 2018, 379(10):958-966, 9 pgs.

Singh, B., et al., "Repetitive intradermal bleomycin injections evoke T-helper cell 2 cytokine-driven pulmonary fibrosis," Am J Physiol Lung Cell Mol Physiol, 2017, 313(5):L796-L806, 11 pgs.

Su, S-A., et al., "Ephrin B2 Regulates Cardiac Fibrosis Through Modulating the Interaction of Stat3 and TGF-β/Smad3 Signaling," Circulation Research, 2017, 121(6): 617-627, 18 pgs.

Wu, X, et al., "Computed Tomographic Biomarkers in Idiopathic Pulmonary Fibrosis. The Future of Quantitative Analysis," Am J Respir Crit Care Med, 2019, 199(1):12-21, 10 pgs.

Yang, G., et al., "Discovery and validation of extracellular/ circulating microRNAs during idiopathic pulmonary fibrosis disease progression," Gene, 2015, 562(1):138-144, 7 pgs.

Young, J.J., et al., "Development of a Protein Biomarker Panel to Detect Non-Small-Cell Lung Cancer in Korea," Clinical Lung Cancer, 2017, 18(2):e99-e107, 9 pgs.

International Search Report and Written Opinion dated Feb. 9, 2021 for Application No. PCT/US2020/054664, 12 pgs.

Abedin, S., et al., "Predictive Value of Bronchiolitis Obliterans Syndrome Stage 0p in Chronic Graft-versus-Host Disease of the Lung," Biol Blood Marrow Transplant, 2015, 21(6):1127-1131, 15 pgs.

Accurso FJ, et al., "Effect of VX-770 in Persons with Cystic Fibrosis and the G551D-CTFR Mutation." N Engl J Med, Nov. 18, 2010, 363(21):1991-2003, 13 pgs.

Ahmed, H., et al., "Emerging Gene Therapies for Genetic Hearing Loss," J Assoc Res Otolaryngol, Aug. 16, 2017, 22 pgs.

Albert PS, et al., "An Approach for Jointly Modeling Multivariate Longitudinal Measurements and Discrete Time-To-Event Data," Ann Appl Stat, 2010, 4(3):1517-1532, 16 pgs.

Altieri, D.C., "Validating Survivin as a Cancer Therapeutic Target," Nat Rev Cancer, 2003, 3(1):46-54, 9 pgs.

Amanat, F., et al., "A serological assay to detect SARS-CoV-2 seroconversion in humans," Nat. Med, 2020, 26(7):1033-1036, 16 pgs.

Arai, H., et al., "Nestin expression in brain tumors: its utility for pathological diagnosis and correlation with the prognosis of high-grade gliomas," Brain Tumor Pathol, 2012, 29(3):160-167, 8 pgs.

Asar O, et al., "mmm: An R package for analyzing multivariate longitudinal data with multivariate marginal models," Comput Methods Programs Biomed, 2013, 112(3):649-654, 6 pgs.

Assi, H., et al., "Gene Therapy for Brain Tumors: Basic Developments and Clinical Implementation," Neurosci Lett, 2012, 527(2):71-77, 14 pgs.

Aurora, P., et al.," Quality Control for Spirometry in Preschool Children with and without Lung Disease," Am J Respir Crit Care Med, 2004, 169:1152-1159, 8 pgs.

Aziz, M.D., et al., "Disease Risk and GVHD Biomarkers Can Stratify Patients For Risk of Relapse and Non-Relapse Mortality Post Hematopoietic Cell Transplant," Leukemia, 2020, 34(7):1898-1906, 17 pgs.

Benden, C., et al., "Therapy options for chronic lung allograft dysfunction-bronchiliolitis obliterans syndrome following first-line immunosuppressive strategies: A systematic review," Journal of Heart and Lung Transplantation, 2017, 36(9):921-933, 13 pgs.

Bergeron, A., et al., "Noninfectious lung complications after allogeneic haematopoietic stem cell transplantation," Eur Respir J, 2018, 51:1702617, 13 pgs.

Bhang, H.-E.C., et al., "Tumor-Specific Imaging Through Progression Elevated Gene-3 Promoter-Driven Gene Expression," Nat Med, 2011, 17(1):123-129, 16 pgs.

Bossen, C., et al., "Interactions of Tumor Necrosis Factor (TNF) and TNF Receptor Family Members in the Mouse and Human," J Biol Chem, 2006, 281(20):13964-13971, 8 pgs.

Brebner JA, et al., "Polyclonal free light chains: a biomarker of inflammatory disease or treatment target?" F1000 Med Rep, 2013, 5:4, 6 pgs.

Brewington, J.J., et al., "Detection of CFTR function and modulation in primary human nasal cell spheroids," J Cyst Fibros, 2018, 17(1):26-33, 17 pgs.

Brody, A.S., et al., "High-Resolution Computed Tomography in Young patients with Cystic Fibrosis: Distribution of Abnormalities and Correlation with Pulmonary Function Tests," J Peds, 2004, 145(1):32-38, 7 pgs.

Bundgaard, H., (ed.), Design of Prodrugs, Elsevier, Amsterdam, 1985, pp. 7-9, 21-24, 8 pgs.

Cai, X., et al., "Gene delivery to mitotic and postmitotic photoreceptors via compacted DNA nanoparticles results in improved phenotype in a mouse model of retinitis pigmentosa," FASEB J, Apr. 2010, 24(4):1178-91, 25 pgs.

Callow, K.A., et al., "The time course of the immune response to experimental coronavirus infection of man," Epidemiol Infect, 1990, 105:435-446, 12 pgs.

Casadevall, A., et al., "The convalescent sera option for containing COVID-19," J Clin Invest, 2020, 130(4):1545-1548,.

Centers for Disease Control and Prevention (CDC) Revised U.S. surveillance case definition for severe acute respiratory syndrome (SARS) and update on SARS cases-United States and worldwide, Dec. 2003. MMWR Morb. Mortal. Wkly. Rep., 2003, 52, 1202-1206, 6 pgs.

Chang, C.-K., et al., "Multiple Nucleic Acid Binding Sites and Intrinsic Disorder of Severe Acute Respiratory Syndrome Coronavirus Nucleocapsid Protein: Implications for Ribonucleocapsid Protein Packaging," J Virol, 2009, 83(5):2255-2264, 10 pgs.

Chassagnon, G., et al., "Long-term computed tomographic changes in cystic fibrosis patients treated with ivacaftor," Eur Respir J, 2016, 48(1):249-252, 4 pgs.

Chatterjee N, et al., "Constrained Maximum Likelihood Estimation for Model Calibration Using Summary-level Information from External Big Data Sources" J Am Stat Assoc, 2016, 111(513):107-117, 11 pgs.

Chen J, et al., "Dysfunction of Nrf-2 in CF Epithelia Leads to Excess Intracellular $H_2O_2$ and Inflammatory Cytokine Production," PLoS One, 2008, 3(10):e3367, 12 pgs.

Chen, X., et al., "Cell Surface Nucleolin Serves as Receptor for DNA Nanoparticles Composed of Pegylated Polylysine and DNA," Mol Ther, 2008, 16(2):333-342, 10 pgs.

Chen X, et al., "Nucleolin-Mediated Cellular Trafficking of DNA Nanoparticle Is Lipid Raft and Microtubule Dependent and Can Be Modulated by Glucocorticoid," Mol Ther, 2011, 19(1):93-102, 10 pgs.

Cheng, G.-S., et al., "Lung Function Trajectory in Bronchiolitis Obliterans Syndrome after Allogeneic Hematopoietic Cell Transplant," Ann Am Thorac Soc, 2016; 13(11):1932-1939, 8 pgs.

Chi, X., et al., "A neutralizing human antibody binds to the N-terminal domain of the Spike protein of SARS-CoV-2," Science, 2020, 369:650-655, 6 pgs.

Chien, J.W., et al., "Bronchiolitis Obliterans Syndrome After Allogeneic Hematopoietic Stem Cell Transplantation: An Increasingly Recognized Manifestation of Chronic Graft-versus-Host Disease," Biol Blood Marrow Transplant, 2010, 16(1):S106-S114, 9 pgs.

Chipman HA, et al., "BART: Bayesian Additive Regression Trees," Ann Appl Stat, 2014, 23(1):42-59, 33 pgs.

Chirkova T, et al., "CX3CR1 is an important surface molecule for respiratory syncytial virus infection in human airway epithelial cells," J Gen Virol, 2015, 96:2543-2556, 14 pgs.

Chmiel J, et al., "The Effect of Sulforaphane in Broccoli Sprouts on Nrf2 Activation, Glutathione, Markers of Oxidative Stress, and Neutrophil Migration," Pediatr Pulmonol, 2012, 47(S35):250; 2012 Cystic Fibrosis Conference, Poster Session Abstract 82*, 1 pg.

Christensen, C.L., et al., "Targeted cytosine deaminase-uracil phosphoribosyl transferase suicide gene therapy induces small cell lung cancer-specific cytotoxicity and tumor growth delay," Clin Cancer Res, 2010, 16(8):2308-2319, 21 pgs.

(56) References Cited

OTHER PUBLICATIONS

Chromy, B.A., et al., "Proteomic Analysis of Human Serum by Two-Dimensional Differential Gel Electrophoresis after Depletion of High-Abundant Proteins," Journal of Proteome Research, 2004, 3:1120-1127, 8 pgs.

Chui, CK, et al., "Interpolation by Multivariate Splines," Math Comput, 1988, 51(183):203-218, 16 pgs.

Clancy JP, et al., "Personalized Medicine in Cystic Fibrosis: Dawning of a New Era," Am J Respir Crit Care Med, 2012, 186(7):593-597, 5 pgs.

Cohen, H.Y., et al., "Calorie Restriction Promotes Mammalian Cell Survival by Inducing the SIRT1 Deacetylase," Science, 2004, 305(5682):390-392.

Cox, D.R., et al., "Large Nos. of explanatory variables, a semi-descriptive analysis," PNAS, 2017, 114(32):8592-8595, 4 pgs.

Dachs, G.U., et al, "From bench to bedside for gene-directed enzyme prodrug therapy of cancer," Anti-Cancer Drugs, 2005, 16(4):349-359, 11 pgs.

De Silva, T., et al., "Markers of rejection of a lung allograft: state of the art," Biomark Med, 2022, 16(6):483-498, 16 pgs.

Debinski, W., et al., "Convection-enhanced delivery for the treatment of brain tumors," Expert Rev Neurother, 2009, 9(10):1519-1527, 15 pgs.

Deboer, E.M., et al., "Proteomic profiling identifies novel circulating markers associated with bronchiectasis in cystic fibrosis," Proteomics Clin Appl, 2017, 11(9-10):1600147, 9 pgs.

Deboer, E.M., et al., "Novel Application of Aptamer Proteomic Analysis in Cystic Fibrosis Bronchoalveolar Lavage Fluid," Proteomics Clin Appl, 2019, 13:1800085, 8 pgs.

Deeks, J.J., et al. "Antibody tests for identification of current and past infection with SARS-CoV-2 (Review)," Cochrane Database Syst Rev, 2020, 6:CD013652, 306 pgs.

Diggle, P.J., et al., "Real-time monitoring of progression towards renal failure in primary care patients," Biostatistics, 2015, 16(3):522-536, 15 pgs.

Dijkman, R., et al., "Human Coronavirus NL63 and 229E Seroconversion in Children," J Clin Microbiol, 2008, 46(7):2368-2373, 6 pgs.

Ding, X.Q., et al., "Ocular delivery of compacted DNA-nanoparticles does not elicit toxicity in the mouse retina," PLoS One, 2009, 4(10):e7410, 11 pgs.

Drumm ML, et al., "Genetic Variation and Clinical Heterogeneity in Cystic Fibrosis," Annu Rev Pathol, 2012, 7:267-282, 18 pgs.

Du, L., et al., "The spike protein of SARS-CoV—a target for vaccine and therapeutic development," Nat Rev Microbiol, 2009, 7:226-236, 11 pgs.

Duan LL, et at., "Bayesian Ensemble Trees (BET) for Clustering and Prediction in Heterogeneous Data," J Comput Graph Stat, 2016, 25(3):748-761, 14 pgs.

Duan LL, et al., "Joint Hierarchical Gaussian Process Model with Application to Forecast in Medical Monitoring," 2014, eprint arXiv:1408.4660, 23 pgs.

Dunn, M., et al., "Pediatric Bone Marrow Transplant Recipients That Develop Bronchiolitis Obliterans Syndrome Exhibit Significant Changes in Complement Activation, Angiotensin Maturation, and Cholesterol Processing Prior to Clinical Diagnosis," Am J Respir Crit Care Med, 2021, 203(9):A3281 (Abstract), 2 pgs.

Eichinger, M., et al., "Morphologic and functional scoring of cystic fibrosis lung disease using MRI," European Journal of Radiology, 2012, 81(6):1321-1329, 9 pgs.

Eroshenko, N., et al., "Implications of antibody-dependent enhancement of infection for SARS-CoV-2 countermeasures," Nat Biotechnol, 2020, 38:789-791, 3 pgs.

Estenne, M., et al., "Bronchiolitis Obliterans Syndrome 2001: An Update of the Diagnostic Criteria," J Heart Lung Transplant, 2002; 21:297-310, 14 pgs.

Fagerland, M.W., et al., "The McNemar test for binary matched-pairs data: mid-p and asymptotic are better than exact conditional," BMC Med Res Methodol, 2013, 13:91, 8 pgs.

Fan, X., et al., "hTERT Gene Amplification and Increased mRNA Expression in Central Nervous System Embryonal Tumors," Am J Pathol, 2003, 162(6):1763-1769, 7 pgs.

Farjo, R., et al., "Efficient non-viral ocular gene transfer with compacted DNA nanoparticles," PLoS One, 2006, 1:e38, 12 pgs.

Feng, S., et al., "Recombinant adenoviral vector expressing human wild-type p53, GM-CSF, and B7-1 genes suppresses the growth of glioma in vivo," Tumor Biol, 2014, 35:441-4417, 7 pgs.

Fieuws S, et al., "Predicting renal graft failure using multivariate longitudinal profiles," Biostatistics, 2008, 9(3):419-431, 13 pgs.

Fieuws S, et al., "Random-effects models for multivariate repeated measures," Stat Methods Med Res, Oct. 2007, 16(5):387-397, 11 pgs.

Fink, Z.W., et al., "PepSIRF: a flexible and comprehensive tool for the analysis of data from highly-multiplexed DNA-barcoded peptide assays," arXiv, 2020, 5 pgs.

Fischer K, et al., "Biomarker Profiling by Nuclear Magnetic Resonance Spectroscopy for the Prediction of All-Cause Mortality: An Observational Study of 17,345 Persons," PLoS Med, Feb. 2014, 11(2):e1001606, 12 pgs.

Fleri, W., et al., "The Immune Epitope Database and Analysis Resource in Epitope Discovery and Synthetic Vaccine Design," Front Immunol, 2017, 8:278, 16 pgs.

Fletcher, A.M., et al., "Transgene expression in the striatum following intracerebral injections of DNA nanoparticles encoding for human glial cell line-derived neurotrophic factor," Neuroscience, Oct. 27, 2011, 194:220-6, 7 pgs.

Fortin, S.P., et al., "Tumor Necrosis Factor-Like Weak Inducer of Apoptosis (TWEAK) Stimulation of Glioma Cell Survival Is Dependent Upon Akt2 Function," Mol Cancer Res, 2009, 7(11):1871-1881, 24 pgs.

Friesen, R.H.E., et al., "A common solution to group 2 influenza virus neutralization," PNAS, 2014, 111(1):445-450, 6 pgs.

Galzio, R., et al., "Glycosilated Nucleolin as Marker for Human Gliomas," J Cell Biochem, 2012, 113(2):571-579, 9 pgs.

Geyer, P.E., et al., "Plasma Proteome Profiling to Assess Human Health and Disease," Cell Syst, 2016, 2:185-195, 12 pgs.

Geyer, P.E., et al., "Proteomics reveals the effects of sustained weight loss on the human plasma proteome," Mol Syst Biol, 2016; 12:901, 16 pgs.

Gorse, G.J., et al., "Prevalence of Antibodies to Four Human Coronaviruses is Lower in Nasal Secretions than in Serum," Clin Vaccine Immunol, 2010, 17(12):1875-1880, 6 pgs.

Gostic, K.M., et al., "Potent Protection against H5N1 and H7N9 Influenza via Childhood Hemagglutinin Imprinting," Science, 2016, 354(6313):722-726, 16 pgs.

Grassi, N., et al., "Ultra-deep and quantitative saliva proteome reveals dynamics of the oral microbiome," Genome Med, 2016, 8:44, 13 pgs.

Green, PJ, et al., "Nonparametric regression and generalized linear models: a roughness penalty approach," 1st ed. London, New York: Chapman & Hall, 1994, ix, 182 p. Table of Contents Only, 8 pgs.

Grifoni, A., et al., "Targets of T Cell Responses to SARS-CoV-2 Coronavirus in Humans with COVID-19 Disease and Unexposed Individuals," Cell, 2020, 181:1489-1501, 29 pgs.

Groot Kormelink, T., et al., "Immunoglobulin Free Light Chains Are Increased in Hypersensitivity Pneumonitis and Idiopathic Pulmonary Fibrosis," PLoS one, 2011, 6(9):e25392, 7 pgs.

Guo, J., et al., "Longitudinal free-breathing MRI measurement of murine lung physiology in a progressive model of lung fibrosis," J Appl Physio, 2019, 126(4):1138-1149, 12 pgs.

Gurunathan, S., et al., "Regulation of Fibroblast Growth Factor-inducible 14 (Fn14) Expression Levels via Ligand-independent Lysosomal Degradation," J Biol Chem, 2014, 289(19):12976-12988, 13 pgs.

Halstead, S.B., et al., "Antibody-enhanced dengue virus infection in primate leukocytes," Nature, 1977, 265:739-741, 3 pgs.

Han, Z., et al., "AAV and Compacted DNA Nanoparticles for the Treatment of Retinal Disorders: Challenges and Future Prospects," Invest Ophthalmol Vis Sci, 2011, 52(6):3051-3059, 9 pgs.

Hanania, N.A., et al., "Acute bronchodilator responsiveness and health outcomes in COPD patients in the UPLIFT trial," Respiratory Research, 2011, 12(1):6, 11 pgs.

(56) References Cited

OTHER PUBLICATIONS

Hansen, J., et al., "Studies in humanized mice and convalescent humans yield a SARS-CoV-2 antibody cocktail," Science, 2020, 369:1010-1014, 5 pgs.

Hartwell, M.J., et al., "An early-biomarker algorithm predicts lethal graft-versus-host disease and survival," JCI Insight, 2017, 2(3):e89798, 9 pgs.

Harun SN, et al., "A systematic review of studies examining the rate of lung function decline in patients with cystic fibrosis," Paediatr Respir Rev, 2016, 20:55-66, 12 pgs.

Hassan, J., et al., "Serum IgA and IGg Subclasses During Treatment for Acute Respiratory Exacerbation in Cystic Fibrosis: Analysis of Patients Colonised with Mucoid or Non-Mucoid Strains of Pseudomonas Aeruginosa," Immunological Investigations, 1994, 23(1):1-13, 14 pgs.

Hastie T, et al., The Elements of Statistical Learning: Data Mining, Inference, and Prediction, Second Ed., Springer Science + Business Media, LLC, New York, NY, 2009, (Table of Contents Only) 12 pgs.

Heijerman, H.G.M., et al., "Efficacy and safety of the elexacaftor/tezacaftor/ivacaftor combination regimen in people with cystic fibrosis homozygous for the F508del mutation: a double-blind, randomised, phase 3 trial," Lancet, 2019, 394(10212):1940-1948, 21 pgs.

Heltshe, S.L., et al., "Ivacaftor-treated Patients with Cystic Fibrosis Derive Long-Term Benefit Despite No Short-Term Clinical Improvement," Am J Respir Crit Care Med, 2018, 197(11):1483-1486, 4 pgs.

Hersh, D.S., et al., "The TNF receptor family member Fn14 is highly expressed in recurrent glioblastoma and in GBM patient-derived xenografts with acquired temozolomide resistance," Neuro Oncol, 2018, 20(10):1321-1330, 10 pgs.

Higano, N.S., et al., "Retrospective respiratory self-gating and removal of bulk motion in pulmonary UTE MRI of neonates and adults," Magn Reason Med, 2017, 77(3):1284-1295, 25 pgs.

Higuchi, T., and V. Stella (Eds.), Pro-drugs as Novel Drug Delivery Systems, ACS Symposium Series 14, American Chemical Society, Washington, D.C., 1975, 6 pgs. [Bibliographic data only].

Hildebrandt, G.C., et al., "Diagnosis and treatment of pulmonary chronic GVHD: report from the consensus confrence on clinical practice in chronic GVHD," Bone Marrow Transplant, 2011, 46(10):1283-1295, 13 pgs.

Hoofnagle, J.H., et al., "Antibody to Hepatitis B Core Antigen. A Sensitive Indicator of Hepatitis B Virus Replication," N Engl J Med, 1974, 290:1336-1340, 5 pgs.

Hoy, S.M., "Elexacaftor/Ivacaftor/Tezacaftor: First Approval," Drugs, 2019, 79(18):2001-2007, 7 pgs.

Huang, J., et al., "CRISPR Editing in Biological and Biomedical Investigation," J Cell Physiol, Aug. 8, 2017, 19 pgs.

Huang, L., et al., "Highly Selective Targeting of Hepatic Stellate Cells for Liver Fibrosis Treatment Using a $_D$-Enantiomeric Peptide Ligand of Fn14 Identified by Mirror-Image mRNA Display," Mol Pharmaceutics, 2017, 14:1742-1753, 12 pgs.

Huttenhain, R., et al., "A Targeted Mass Spectrometry Strategy for Developing Proteomic Biomarkers: A Case Study of Epithelial Ovarian Cancer," Mol Cell Proteomics, 2019, 18:1836-1850, 16 pgs.

Jagasia, M.H., et al., "National Institutes of Health Consensus Development Project on Criteria for Clinical Trials in Chronic Graft-versus-Host Disease: I. The 2014 Diagnosis and Staging Working Group Report," Biol Blood Marrow Transplant, 2015, 21(3):389-401.el, 27 pgs.

James GM, et al., "Principal component models for sparse functional data," Biometrika, 2000, 87(3):587-602, 16 pgs.

Jia, N., et al., "Emergence of human infection with Jingmen tick virus in China: A retrospective study," EBioMedicine, 2019, 43:317-324, 8 pgs.

Jiang C-R, et al., "Covariate Adjusted Functional Principal Components Analysis for Longitudinal Data," The Annals of Statistics, 2010, 38(2): 1194-1226, 34 pgs.

Jiang, X., et al., "The Imprinted Gene PEG3 Inhibits Wnt Signaling and Regulates Glioma Growth," J Biol Chem, 2010, 285(11):8472-8480, 9 pgs.

Jodele, S., et al., "Complement blockade for TA-TMA: lessons learned from a large pediatric cohort treated with eculizumab," Blood, 2020, 135(13):1049-1057, 9 pgs.

Jodele, S., et al., "Interferon-complement loop in transplant-associated thrombotic microangiopathy," Blood Adv, 2020, 4(6):1166-1177, 12 pgs.

Joo, K.M., et al., "Patient-Specific Orthotopic Glioblastoma Xenograft Models Recapitulate the Histopathology and Biology of Human Glioblastomas In Situ," Cell Rep, 2013, 3(1):260-273, 14 pgs.

Kajiwara, Y., et al., "Expression of Survivin in Astrocytic Tumors: Correlation with Malignant Grade and Prognosis," Cancer, 2003, 97(4):1077-1083, 7 pgs.

Kall, L., et al., "Semi-supervised learning for peptide identification from shotgun proteomics datasets," Nat Methods, 2007, 4(11):923-925, 3 pgs.

Katzelnick, L.C., et al., "Antibody-dependent enhancement of severe dengue disease in humans," Science, 2017, 358:929-932, 4 pgs.

Keng, C.-T., et al., "Amino Acids 1055 to 1192 in the S2 Region of Severe Acute Respiratory Syndrome Coronavirus S Protein Induce Neutralizing Antibodies: Implications for the Development of Vaccines and Antiviral Agents," J Virol, 2005, 79(6):3289-3296, 8 pgs.

Keogh, R.H., et al., "Dynamic Predication of Survival in Cystic Fibrosis: A Landmarking Analysis Using UK Patient Registry Data," Epidemiology, 2019, 30(1):29-37, 9 pgs.

Khan, S., et al., "Analysis of Serologic Cross-Reactivity Between Common Human Coronaviruses and SARS-CoV-2 Using Coronavirus Antigen Microarray," bioRxiv, 2020, 10 pgs.

Khurana, S., et al., "Vaccine-Induced Anti-HA2 Antibodies Promote Virus Fusion and Enhance Influenza Virus Respiratory Disease," Sci Transl Med, 2013, 5(200):200ra114, 10 pgs.

Kibbey, M.C., et al., "A 110-kD Nuclear Shuttling Protein, Nucleolin, Binds to the Neurite-Promoting IKVAV Site of Laminin-1," J Neurosci Res, 1995, 42(3):314-322, 9 pgs.

Kim PY, et al., "Identification of plasma Complement C3 as a potential biomarker for neuroblastoma using a quantitative proteomic approach," J Proteomics, 2014, 96:1-12, 12 pgs.

King, T.E., et al., "A Phase 3 Trial of Pirfenidone in Patients with Idiopathic Pulmonary Fibrosis," N Engl J Med, 2014, 370(22):2083-2092, 10 pgs.

Koirala, A., et al., "S/MAR-containing DNA nanoparticles promote persistent RPE gene expression and improvement in RPE65-associated LCA," Hum Mol Genet, Apr. 15, 2013, 22(8):1632-42, 11 pgs.

Kolodziej, M., et al., "Roscotirine has anti-proliferative and pro-apoptotic effects on glioblastoma cell lines: A pilot study," Oncology Reports, 2015, 34:1549-1556, 8 pgs.

Konstan, M.W., et al., "Assessment of safety and efficacy of long-term treatment with combination lumacaftor and ivacaftor therapy in patients with cystic fibrosis homozygous for the F508del-CFTR mutation (PROGRESS): a phase 3, extension study," Lancet Respir Med, 2017, 5(2):107-118, 12 pgs.

Konstan, M.W., et al., "Compacted DNA nanoparticles administered to the nasal mucosa of cystic fibrosis subjects are safe and demonstrate partial to complete cystic fibrosis transmembrane regulator reconstitution," Hum. Gene Ther., Dec. 2004, 15(12):1255-69, 15 pgs.

Konstan, M.W., et al., "Risk Factors for Rate of Decline in Forced Expiratory Volume in One Second in Children and Adolescents with Cystic Fibrosis," J Pediatr, 2007, 151(2): 134- 139e1, 7 pgs.

Konstan, M.W., et al., "Risk Factors for Rate of Decline in FEV1 in Adults with Cystic Fibrosis," J Cyst Fibros, 2012, 11(5):405-411, 15 pgs.

Kozlov, I.A., et al., "A Highly Scalable Peptide-Based Assay System for Proteomics," PLoS One, 2012, 7(6):e37441, 10 pgs.

Krammer, F., et al., "Serology assays to manage COVID-19: Measurement of antibodies to SAR-CoV-2 will improve disease management if used correctly," Science, 2020, 368(6495):1060-1061, 2 pgs.

(56)     References Cited

OTHER PUBLICATIONS

Krisp, C., et al., "Proteomic phenotyping of metastatic melanoma reveals putative signatures of MEK inhibitor response and prognosis," Br J Cancer, 2018; 119:713-723, 11 pgs.

Ku, N-O., et al., "Mutation of Human Keratin 18 in Association with Cryptogenic Cirrhosis," J Clin Invest, 1997, 99(1):19-23, 5 pgs.

La Rosa PS, et al., "Hypothesis Testing and Power Calculations for Taxonomic-Based Human Microbiome Data," PLoS One, 2012, 7(12):e52078, 13 pgs.

Laguna, TA, et al., "Sputum Desmosine During Hospital Admission for Pulmonary Exacerbation in Cystic Fibrosis," Chest, Dec. 2009, 136(6):1561-1568, 8 pgs.

Lai, S.-C., et al., "Characterization of neutralizing monoclonal antibodies recognizing a 15-residues epitope on the spike protein HR2 region of severe acute respiratory syndrome coronavirus (SARS-CoV)," J Biomed Sci, 2005, 12:711-727, 17 pgs.

Lancioni, CL, et al., "*Mycobacterium tuberculosis* Lipoproteins Directly Regulate Human Memory CD4+ T Cell Activation via Toll-Like Receptors 1 and 2," Infect Immun, Feb. 2011, 79(2):663-673, 11 pgs.

Larman, H.B., et al. "Application of a synthetic human proteome to autoantigen discovery through PhIP-Seq," Nat Biotechnol, 2011, 29(6):535-541, 19 pgs.

Le, T.T., et al., "The COVID-19 vaccine development landscape," Nat Rev Drug Discov, 2020, 19:305-306, 2 pgs.

Lederer, D.J., et al., "Control of Confounding and Reporting of Results in Casual Inference Studies: Guidance for Authors form Editors of Respiratory, Sleep, and Critical Care Journals," Ann Am Thorac Soc, 2019, 16(1):22-28, 8 pgs.

Lederlin, M., et al., "Three-Dimensional Assessment of Lung Tissue Density Using a Clinical Ultrashort Echo Time at 3 Tesla: A Feasibility Study in Healthy Subjects," J Magn Reson Imag, 2014, 40(4):839-847, 9 pgs.

Li, A., et al., "Unsupervised Analysis of Transcriptomic Profiles Reveals Six Glioma Subtypes," Cancer Res, 2009, 69(5):2091-2099, 17 pgs.

Li, D., et al., "Flexible semiparametric joint modeling: an application to estimate individual long function decline and risk of pulmonary exacerbations in cystic fibrosis," Emerg Themes Epidemiol, 2017, 14:13, 13 pgs.

Li, Q, et al., "Rv2468c, a novel *Mycobacterium tuberculosis* protein that costimulates human CD4+ T cells through VLA-5," J Leukoc Biol, Feb. 2012, 91(2):311-20, 10 pgs.

Liou, TG, et al., "Year-to-year changes in lung function in individuals with cystic fibrosis," J Cyst Fibros, 2010, 9(4):250-6, 7 pgs.

Liu, A., et al., "Antibody responses against SARS-CoV-2 in COVID-19 patients," J Med Virol, 2021, 93:144-148, 5 pgs.

Liu, G., et al., "Nanoparticles of Compacted DNA Transfect Postmitotic Cells," J Biol Chem, 2003, 278(35):32578-32586, 9 pgs.

Liu, S., et al., "Interaction between heptad repeat 1 and 2 regions in spike protein of SARS- associated coronavirus: implications for virus fusogenic mechanism and identification of fusion inhibitors," Lancet, 2004, 363:938-947, 10 pgs.

Liu, X., et al., "Proteomic Characterization Revels That MMP-3 Correlates With Bronchiolititis Obliterans Syndrome Following Allogeneic Hematopoietic Cell and Lung Transplantation," Am J Transplant, 2016, 16(8):2342-2351, 28 pgs.

Loew, W., et al., "A Volume Saddle Coil for Hyperpolarized 129Xe Lung Imaging," Proc Int Soc Magn Reson Med, 2015, 23:1507, 1 pg. [Abstract only].

Lounder, D.T., et al., "Lower levels of vitamin A are associated with increased gastrointestinal graft-versus-host disease in children," Blood, 2017, 129(20):2801-2807, 7 pgs.

Lu, R., et al., "Genomic characterisation and epidemiology of 2019 novel coronavirus: implications for virus origins and receptor binding," Lancet, 2020, 395:565-574, 10 pgs.

Lubroth, J., et al., "Absence of protein 2C from clarified foot-and-mouth disease virus vaccines provides the basis for distinguishing convalescent from vaccinated animals," Vaccine, 1996, 14(5):419-427, 9 pgs.

Lucchese, G., et al., "Peptidology: short amino acid modules in cell biology and immunology," Amino Acids, 2007, 33:703-707, 5 pgs.

Luebbering, N., et al., "Endothelial injury, F-actin and vitamin D binding protein after hematopoietic stem cell transplant and association with clinical outcomes," Haematologica, 2021, 106(5):1321-1329, 9 pgs.

Lv, H., et al., "Cross-reactive Antibody Response between SARS-CoV-2 and SARS-CoV Infections," Cell Rep, 2020, 31:107725, 10 pgs.

Major-Monfried, H., et al., "MAGIC biomarkers predict long-term outcomes for steroid-resistant acute GVHD," Blood, 2018, 131(25):2846-2855, 10 pgs.

Martens, T., et al., "Inhibition of Glioblastoma Growth in a Highly Invasive Nude Mouse Model Can Be Achieved by Targeting Epidermal Growth Factor Receptor but not Vascular Endothelial Growth Factor Receptor-2," Clin Cancer Res, 2008, 14(17):5447-5458, 12 pgs.

Mastorakos, P., et al., "Highly PEGylated DNA Nanoparticles Provide Uniform and Widespread Gene Transfer in the Brain," Adv Healthc Mater, 2015, 4(7):1023-1033, 24 pgs.

Mead, B.P., et al., "Novel Focused Ultrasound Gene Therapy Approach Noninvasively Restores Dopaminergic Neuron Function in a Rat Parkinson's Disease Model," Nano Lett, 2017, 17(6):3533-3542, 21 pgs.

Middleton, P.G., et al., "Elexacaftor-Tezacaftor-Ivacaftor for Cystic Fibrosis with a Single Phe508del Allele," N Engl J Med, 2019, 381(19):1809-1819, 16 pgs.

Miller, G.W., et al., "Hyperpolarized 3He lung ventilation imaging with B1-inhomogeneity correction in a single breath-hold scan," MAGMA, 2004, 16(5):218-226, 9 pgs.

Mina, M.J., et al., "Measles virus infection diminishes preexisting antibodies that offer protection from other pathogens," Science, 2019, 366(6465):599-606, 18 pgs.

Monto, A.S., et al., "The Doctrine of Original Antigenic Sin: Separating Good From Evil," J Infect Dis, 2017, 215:1782-1788, 7 pgs.

Muhlebach, M.S, et al., "Biomarkers for Cystic Fibrosis Drug Development," J Cyst Fibros, 2016, 15(6):714-723, 20 pgs.

Nance, E.A., et al., "A Dense Poly(ethylene glycol) Coating Improves Penetration of Large Polymeric Nanoparticles within Brain Tissue," Sci Transl Med, 2012, 4(149):149ra119, 18 pgs.

Naso, M.F., et al., "Adeno-Associated Virus (AAV) as a Vector for Gene Therapy," Bio Drugs, Jul. 1, 2017, 31:317-334, 18 pgs.

Negroni, L., et al., "Treatment of colon cancer cells using the cytosine deaminase/5-fluorocytosine suicide system induces apoptosis, modulation of the proteome, and Hsp90β phosphorylation," Mol Cancer Ther, 2007, 6(10):2747-2756, 10 pgs.

Ni, L., et al., "Detection of SARS-CoV-2-Specific Humoral and Cellular Immunity in COVID-19 Convalescent Individuals," Immunity, 2020, 52:971-977, 11 pgs.

Nichols, D.P., et al., "The triterpenoid CDDO limits inflammation in preclinical models of cystic fibrosis lung disease," Am J Physiol Lung Cell Mol Physiol, 2009, 297(5):L828-L836, 9 pgs.

Nick Ja, et al., "Blood mRNA biomarkers for detection of treatment response in acute pulmonary exacerbations of cystic fibrosis," Thorax, 2013, 68(10):929-937, 9 pgs.

Nie, J., et al., "Establishment and validation of a pseudovirus neutralization assay for SARS-CoV-2," Emerg Microbes Infect, 2020, 9:680-686, 7 pgs.

Niedbalski, P.J., et al., "Mapping and correcting hyperpolarized magnetization decay with radial keyhole imaging," Magn Reson Med, 2019, 82:367-376, 10 pgs.

Obuchowski Na, et al., "Sample Size Determination for Diagnostic Accuracy Studies Involving Binormal ROC Curve Indices," Stat Med, 1997, 16(13):1529-1542, 14 pgs.

O'Mahony, A.M., et al., "Non-viral Nanosystems for Gene and Small Interfering RNA Delivery to the Central Nervous System: Formulating the Solution," J Pharm Sci, 2013, 102(10):3469-3484, 16 pgs.

Ostrom, Q.T., et al., "CBTRUS Statistical Report: Primary Brain and Central Nervous System Tumors Diagnosed in the United States in 2006-2010," Neuro-Oncol, 2013, 15(Suppl 2):ii1-ii56, 56 pgs.

(56) References Cited

OTHER PUBLICATIONS

Patrizii, M., et al., "Utility of Glioblastoma Patient-Derived Orthotopic Xenografts in Drug Discovery and Personalized Therapy," Front Oncol, 2018, 8:article 23, 9 pgs.

Pearce, M.S., et al., "Radiation exposure from CT scans in childhood and subsequent risk of leukaemia and brain tumours: a retrospective cohort study," Lancet, 2012, 380(9840):499-505, 7 pgs.

Peila, C., et al., "Effects of Holder pasteurization on the protein profile of human milk," Italian journal of Pediatrics, 2016, 42:36, 8 pgs.

Pelekanou, V., et al., "BAFF, APRIL, TWEAK, BCMA, TACI and Fn14 Proteins Are Related to Human Glioma Tumor Grade: Immunohistochemistry and Public Microarray Data Meta-Analysis," PLoS One, 2013, 8(12):e83250, 11 pgs.

Peng, J., et al., "A Geometric Approach to Maximum Likelihood Estimation of the Functional Principal Components From Sparse Longitudinal Data," J Comput Graph Stat, 2009, 18(4):995-1015, Technical Report 2007a, 87 pgs.

Peng, J., Restricted MLE for Functional Principal Components Analysis (R package fpca) 2015. Available from: https://CRAN.R-project.org/package=fpca, 12 pgs.

Perez, J.G., et al., "The TWEAK Receptor Fn14 is a Potential Cell Surface Portal for Targeted Delivery of Glioblastoma Therapeutics," Oncogene, 2016, 35(17):2145-2155, 27 pgs.

Phillips, H.S., et al., "Molecular subclasses of high-grade glioma predict prognosis, delineate a pattern of disease progression, and resemble stages in neurogenesis," Cancer Cell, 2006, 9(3):157-173, 17 pgs.

Pillay, T.S., "Gene of the month: the 2019-nCoV/SARS-CoV-2 novel coronavirus spike protein," J Clin Pathol, 2020, 73:366-369, 4 pgs.

Pinto, D., et al., "Cross-neutralization of SARS-CoV-2 by a human monoclonal SARS-CoV antibody," Nature, 2020, 583:290-295, 22 pgs.

Pipe, J.G., et al., "A New Design and Rationale for 3D Orthogonally Oversampled k-Space Trajectories," Magn Reson Med, 2011, 66(5):1303-1311, 9 pgs.

Poh, C.M., et al., "Two linear epitopes on the SARS-CoV-2 spike protein that elicit neutralising antibodies in COVID-19 patients," Nat Commun, 2020, 11:2806, 7 pgs.

Portsmouth, D., et al., "Suicide genes for cancer therapy," Mol Aspects Med, 2007, 28(1):4-41, 38 pgs.

Price, J.V., et al., "'On silico' peptide microarrays for high-resolution mapping of antibody epitopes and diverse protein-protein interactions," Nat Med, 2012, 18(9):14341440, 16 pgs.

The R Core Team, "R: A Language and Environment for Statistical Computing, R Version 3.5.2" Vienna, Austria, R Foundation for Statistical Computing, 2018, https://www/R-project.org/, 3636 pgs.

Ramsay Jo, et al., *Functional data analysis*, Second Ed., Springer Science + Business Media, Inc., New York., NY, 2005, p. 426, (Table of Contents only) 13 pgs.

Ratjen F, et al., "Effect of Azithromycin on Systemic Markers of Inflammation in Patients With Cystic Fibrosis Uninfected With *Pseudomonas aeruginosa*," Chest, 2012, 142(5):1259-1266, 8 pgs.

Redgate, E.S., et al., "Time of Death of CNS Tumor-Bearing Rats Can Be Reliably Predicted by Body Weight-Loss Patterns," Lab Anim Sci, 1991, 41(3):269-273, 5 pgs.

Roach, D.J., et al., "Ultrashort Echo-Time Magnetic Resonance Imaging Is a Sensitive Method for the Evaluation of Early Cystic Fibrosis Lung Disease," Ann Am Thorac Soc., 2016, 13(11):1923-1931, 9 pgs.

Robbiani, D.F., et al., "Convergent Antibody Responses to SARS-CoV-2 in Convalescent Individuals," Nature, 2020, 584(7821):437-442, 35 pgs.

Robison, R.K., et al., "Three-Dimensional Ultrashort Echo-Time Imaging Using a FLORET Trajectory," Magn Reson Med, 2017, 78(3):1038-1049, 12 pgs.

Roche, E.B., (Ed.), *Bioreversible Carriers in Drug Design: Theory and Application*, American Pharmaceutical Association, 1987, Pergamon Press, New York, 4 pgs. [Table of Contents only].

Rosenfeld M, et al., "Baseline Characteristics and Factors Associated With Nutritional and Pulmonary Status at Enrollment in the Cystic Fibrosis EPIC Observational Cohort," Pediatr Pulmonol, 2010, 45(9):934-944, 11 pgs.

Rosenfeld M, et al., "Decline in Lung Function Does not Predict Future Decline in Lung Function in Cystic Fibrosis Patients," Pediatr Pulmonol, 2015, 50(9):856-862, 7 pgs.

Routledge, E., et al., "Analysis of Murine Coronavirus Surface Glycoprotein Functions by Using Monoclonal Antibodies," J Virol, 1991, 65(1):254-262, 9 pgs.

Rowe, S.M., et al., "Clinical Mechanism of the Cystic Fibrosis Transmembrane Conductance Regulator Potentiator Ivacaftor in G551D-mediated Cystic Fibrosis," Am J Respir Crit Care Med, 2014, 190(2):175-184, 10 pgs.

Rubin, D.B., "Inference and Missing Data," Biometrika, 1976, 63(3):581-592, 12 pgs.

Sagel SD, et al., "Effect of Treatment of Cystic Fibrosis Pulmonary Exacerbations on Systemic Inflammation," Ann Am Thorac Soc, 2015, 12(5):708-717, 10 pgs.

Sagel SD, et al., "Validation of Candidate Serum Protein and Lipid Markers of Disease Severity in CF," Pediatr Pulmonol, 2014, 49(S38):288, 2014 Cystic Fibrosis Conference, Poster Session Abstract 205*, 1 pg.

Sanders DB, et al., "Failure to Recover to Baseline Pulmonary Function after Cystic Fibrosis Pulmonary Exacerbation," Am J Respir Crit Care Med, 2010, 182(5):627-632, 6 pgs.

Saucier-Sawyer, J.K., et al., "Distribution of Polymer Nanoparticles by Convection-Enhanced Delivery to Brain Tumors," J Control Release, 2016, 232:103-112, 26 pgs.

Sausville, E.A. et al, "Contributions of Human Tumor Xenografts to Anticancer Drug Development," Cancer Res, 2006, 66(7):3351-3354, discussion 3354, 4 pgs.

Sawicki, G.S., et al., "Sustained Benefit from Ivacaftor Demonstrated by Combining Clinical Trial and Cystic Fibrosis Patient Registry Data," Am J Respir Crit Care Med, 2015, 192(7):836-842, 7 pgs.

Schaad, U.B., et al., "Serotype-Specific Serum IgG Antibodies to Lipopolysaccharides of *Pseudomonas aeruginosa* in Cystic Fibrosis: Correlation to Disease, Subclass Distribution, and Experimental Protective Capacity," Pediatric Research, 1990, 27(5):508-513, 6 pgs.

Schluchter, M.D., et al., "Classifying Severity of Cystic Fibrosis Lung Disease Using Longitudinal Pulmonary Function Data," Am J Respir Crit Care Med, 2006, 174(7):780-786, 7 pgs.

Schluchter, M.D., et al., "Jointly modelling the relationship between survival and pulmonary function in cystic fibrosis patients," Stat Med, 2002, 21:1271-1287, 17 pgs.

Schwartzbaum, J.A., et al., "Epidemiology and molecular pathology of glioma," Nat Clin Pract Neurol, 2006, 2(9):494-503, 10 pgs.

Shirahata, M., et al., "Gene Expression-Based Molecular Diagnostic System for Malignant Gliomas Is Superior to Histological Diagnosis," Clin Cancer Res, 2007, 13(24):7341-7356, 16 pgs.

Shirahata, M., et al., "Using gene expression profiling to identify a prognostic molecular spectrum in gliomas," Cancer Sci, 2009, 100(1):165-172, 8 pgs.

Shirakawa, T., et al., "Cytotoxicity of Adenoviral-Mediated Cytosine Deaminase Plus 5-Fluorocytosine Gene Therapy is Superior to Thymidine Kinase Plus Acyclovir in a Human Renal Cell Carcinoma Model," J Urol, 1999, 162(3 Pt 1):949-954, 6 pgs.

Shiryaev, S.A., et al., "New Details of HCV NS3/4A Proteinase Functionality Revealed by a High-Throughput Cleavage Assay," PLoS One, 2012, 7(4):e35759, 12 pgs.

Sinha C, et al., "PKA and actin play critical roles as downstream effectors in MRP4-mediated regulation of fibroblast migration," Cell Signal, 2015, 27(7):1345-1355, 11 pgs.

Sinha C, et al., "Capturing the Direct Binding of CFTR Correctors to CFTR by Using Click Chemistry," Chembiochem, 2015, 16:2017-2022, 6 pgs.

Slobodianik NH, et al., "Inflammatory biomarker profile in children with cystic fibrosis: preliminary study," Proc Nutr Soc, 3rd Inter-

(56) References Cited

OTHER PUBLICATIONS national Immunonutrition Workshop; Session 4: Dietary strategies to prevent and mitigate inflammatory diseases, 2010, 69(3):354-356, 3 pgs.

Soares, H.D., et al., "Biomarkers Associated With the Apolipoprotein E Genotype and Alzheimer Disease," Arch Neurol, 2012, 69(10):1310-1317, 16 pgs.

Soundararajan, S., et al., "Plasma Membrane Nucleolin Is a Receptor for the Anticancer Aptamer AS1411 in MV4-11 Leukemia Cells," Mol Pharmacol, 2009, 76(5):984-991, 8 pgs.

Spivak, M., et al., "Improvements to the Percolator algorithm for peptide identification from shotgun proteomics data sets," J Proteome Res, 2009, 8(7):3737-3745, 22 pgs.

Srinagesh, H.K., et al., "The MAGIC algorithm probability is a validated response biomarker of treatment of acute graft-versus-host disease," Blood Advances, 2019, 3(23):4034-4042, 9 pgs.

Stanojevic, S., et al., "Physiologic endpoints for clinical studies for cystic fibrosis," J Cyst Fibros, 2016, 15(4):416-423, 8 pgs.

Su, W., et al., "An empirical comparison of segmented and stochastic linear mixed effects models to estimate rapid disease progression in longitudinal biomarker studies," Stat Biopharm Res, 2021, 13(3):270-279, 22 pgs.

Sun, W., et al., "Real-Time Imaging of Gene Delivery and Expression with DNA Nanoparticle Technologies," Chapter 33, In: Foote R., Lee J. (eds) Micro and Nano Technologies in Bioanalysis. Methods in Molecular Biology (Methods and Protocols), Humana Press, Totowa, NJ Methods Mol Biol, 2009, 544:525-546, 22 pgs.

Szczesniak, R.D., et al., "A semiparametric approach to estimate rapid lung function decline in cystic fibrosis," Annals of Epidemiology, 2013, 23(12):771-777, 7 pgs.

Szczesniak, R.D., et al., "Dynamic predictive probabilities to monitor rapid cystic fibrosis disease progression," Statistics in Medicine, 2020, 39(6):740-756, 17 pgs.

Szczesniak, R.D., et al., "Improving Detection of Rapid Cystic Fibrosis Disease Progression—Early Translation of a Predictive Algorithm Into a Point-of-Care Tool" IEEE Journal of Translational Engineering in Health and Medicine, Point-of-Care Technologies, 2019, 7:2800108, 8 pgs.

Szczesniak, R.D., et al., "Phenotypes of Rapid Cystic Fibrosis Lung Disease Progression during Adolescence and Young Adulthood," American Journal of Respiratory and Critical Care Medicine, 2017, 196(4): 471-478, 8 pgs.

Szczesniak, R.D., et al., "Predicting Future Lung Function Decline in Cystic Fibrosis Patients: Statistical Methods and Clinical Connections," Pediatr Pulmonol, Letter to the Editor, 2016, 51(2):217-218, 2 pgs.

Szczesniak, R., et al., "Use of $FEV_1$ in Cystic Fibrosis Epidemiologic Studies and Clinical Trials: A Statistical Perspective for the Clinical Researcher," J Cyst Fibros, 2017, 16(3):318-326, 17 pgs.

Taillandier, L., et al., "Models for neuro-oncological preclinical studies: solid orthotopic and heterotopic grafts of human gliomas into nude mice," J Neurosci Methods, 2003, 125(1-2):147-157, 11 pgs.

Tamburro, R.F., et al., "Pulmonary Complications of Pediatric Hematopoietic Cell Transplantation: A National Institutes of Health Workshop Summary," Ann Am Thorac Soc, 2021, 18(3):381-394, 14 pgs.

Tan, C.W., et al., "A SARS-CoV-2 surrogate virus neutralization test based on antibody-mediated blockage of ACE2-spike protein-protein interaction," Nat Biotech, 2020, 38:1073-1078, 17 pgs.

Tang Y, et al., "Developing Adaptive Personalized Therapy for Cystic Fibrosis Using Reinforcement Learning," Submitted to Ann Appl Stat, 2012, 28 pgs.

Taylor-Robinson D, et al., "Understanding the natural progression in %FEV1 decline in patients with cystic fibrosis: a longitudinal study," Thorax, 2012, 67(10):860-866, 7 pgs.

Tepper, L.A., et al., "The development of bronchiectasis on chest computed tomography in children with cystic fibrosis: can pre-stages be identified?" Eur Radiol, 2016, 26(12):4563-4569, 7 pgs.

Thomen, R.P., et al., "Hyperpolarized $^{129}$Xe for investigation of mild cystic fibrosis lung disease in pediatric patients," J Cyst Fibros, 2017, 16(2):275-282, 8 pgs.

Tibshirani, R.J., "Regression Shrinkage and Selection via the Lasso," J R Statist Soc B, 1996, 58(1):267-288, 22 pgs.

Tissot, A., et al., "Early Identification of Chronic Lung Allograft Dysfunction: The Need of Biomarkers," Frontiers in Immunology, 2019, 10:Article 1681, 13 pgs.

Tobias, A., et al., "The art of gene therapy for glioma: a review of the challenging road to the bedside," J Neurol Neurosurg Psychiatry, 2013, 84(2):213-222, 20 pgs.

Tran, N.L., et al., "Increased Fibroblast Growth Factor-Inducible 14 Expression Levels Promote Glioma Cell Invasion via Rac1 and Nuclear Factor-κB and Correlate with Poor Patient Outcome," Cancer Res, 2006, 66(19):9535-9542, 8 pgs.

Tran, N.L., et al., "The Human Fn14 Receptor Gene Is Up-Regulated in Migrating Glioma Cells in Vitro and Overexpressed in Advanced Glial Tumors," Am J Pathol, 2003, 162(4):1313-1321, 9 pgs.

Trinh, Q.T., et al., "Enzyme/Prodrug Gene Therapy: Comparison of Cytosine Deaminase/5-Fluorocytosine Versus Thymidine Kinase/Ganciclovir Enzyme/Prodrug Systems in a Human Colorectal Carcinoma Cell Line," Cancer Res, 1995, 55(21):4808-4812, 5 pgs.

Tucholska M, et al., "Human Serum Proteins Fractionated by Preparative Partition Chromatography Prior to LC-ESI-MS/MS," J Proteome Res, 2009, 8(3):1143-1155, 13 pgs.

Uhl Ving, H.H., et al., "Bronchiolitis obliterans after allo-SCT: clinical criteria and treatment options," Bone Marrow Transplantation, 2012, 47:1020-1029, 10 pgs.

Van Der Ploeg, E.A., et al., "The potenial of biomarkers of fibrosis in chronic lung allograft dysfunction," Transplantation Reviews, 2021, 35(3):100626, 11 pgs.

Veraar, C., et al., "Potential novel biomarkers for chronic lung allograft dysfunction and azithromycin responsive allograft dysfunction," Scientific Reports, 2021, 11(1):6799, 13 pgs.

Verbeke G, et al., "The analysis of multivariate longitudinal data: A review," Stat Methods Med Res, 2014, 23(1):42-59, 18 pgs.

Verhaeghe, C., et al., "Intrinsic pro-angiogenic status of cystic fibrosis airway epithelial cells," BioChemical and Biophysical Research Communications, 2007, 356:745-749, 5 pgs.

Verleden, G.M., et al., "Azithromycin Reduces Airway Neutrophilia and Interleukin-8 in Patients with Brochiolitis Obliterans Syndrome," Am J Respir Crit Care Med, 2006, 174:556-570, 5 pgs.

Verleden, S.E., et al., "Chronic lung allograft dysfunction phenotypes and treatment," Journal of Thoracic Disease, 2017, 9(8):2650-2659, 11 pgs.

Vestbo, J., et al., "Natural history of COPD: Focusing on change in FEV1," Respirology, 2016, 21(1):34-43, 10 pgs.

Vogelbaum, M.A et al., "Convection-enhanced delivery for the treatment of glioblastoma," Neuro-Oncol, 2015, 17(Suppl 2):ii3-ii8, 6 pgs.

Volkova, N., et al., "Disease progression in patients with cystic fibrosis treated with ivacaftor: Data from national US and UK registries," J Cystic Fibros, 2020, 19:68-79, 12 pgs.

Wainwright CE, et al., "Lumacaftor-Ivacaftor in Patients with Cystic Fibrosis Homozygous for Phe508del CFTR," N Engl J Med, 2015, 373(3):220-231, 12 pgs.

Walkup, L.L., et al., "Feasibility, tolerability and safety of pediatric hyperpolarized 129Xe magnetic resonance imaging in healthy volunteers and children with cystic fibrosis," Pediatr Radiol, 2016, 46(12):1651-1662, 23 pgs.

Walkup, L.L., et al., "Xenon-129 MRI detects ventilation deficits in pediatric stem-cell transplant patients unable to perform spirometry," Eur Respir J, 2019, 53(5):1-16, 16 pgs.

Walls, A.C., et al., "Tectonic conformational changes of a coronavirus spike glycoprotein promote membrane fusion," PNAS, 2017, 114(42):11157-11162, 6 pgs.

Wang J, et al., "Measuring the impact of apnea and obesity on circadian activity patterns using functional linear modeling of actigraphy data," J Circadian Rhythms, 2011, 9(1):11, 10 pgs.

Wang X, et al., "Hsp90 Cochaperone Aha1 Downregulation Rescues Misfolding of CFTR in Cystic Fibrosis," Cell, 2006, 127(4):803-815, 13 pgs.

(56) References Cited

OTHER PUBLICATIONS

Waterhouse, A., et al., "SWISS-MODEL: homology modelling of protein structures and complexes," Nucleic Acids Res, 2018, 46:W296-W303, 8 pgs.

Wewer Albrechtsen, N.J., et al., "Plasma Proteome Profiling Reveals Dynamics of Inflammatory and Lipid Homeostasis Markers after Roux-En-Y Gastric Bypass Surgery," Cell Syst, 2018, 7:601-612. el-e3, 16 pgs.

Whitman, J.D., et al., "Test performance evaluation of SARS-CoV-2 serological assays," Nat Biotechnol, 2020, 38(10):1174-1183, 26 pgs.

Wielputz, M.O., et al., "Magnetic Resonance Imaging Detects Changes in Structure and Perfusion, and Response to Therapy in Early Cystic Fibrosis Lung Disease," Am J Respir Crit Care Med, 2014, 189(8):956-965, 10 pgs.

Wilcoxon, F., "Individual Comparisons of Grouped Data by Ranking Methods," Journal of Economic Entomology, 1946, 39(2):269-270, 2 pgs.

Willmering, M.M., et al., "Implementation of the FLORET Ultrashort Echo-Time Sequence for Lung Imaging," Magn Reson Med, 2019, 82(3):1091-1100, 17 pgs.

Willmering, M.M., et al., "Improved pulmonary [129]Xe ventilation imaging via 3D-spiral UTE MRI," Magn Reson Med, 2020, 84(1):312-320, 14 pgs.

Winkles, J.A., "The TWEAK-Fn14 cytokine-receptor axis: discovery, biology and therapeutic targeting," Nat Rev Drug Discov, 2008, 7(5):411-425, 32 pgs.

Wolff, D., et al., "Biomarkers in chronic graft-versus-host disease—quo vadis?" Bone Marrow Transplant, 2018, 53(7):832-837, 10 pgs.

Workman, P., et al., "Guidelines for the welfare and use of animals in cancer research," Br J Cancer, 2010, 102(11):1555-1577, 23 pgs.

Xia, S., et al., "A pan-coronavirus fusion inhibitor targeting the HR1 domain of human coronavirus spike," Sci Adv, 2019, 5:eaav4580, 15 pgs.

Xu, G.J., et al., "Comprehensive serological profiling of human populations using a synthetic human virome," Science, 2015, 348(6239):aaa0698, 23 pgs.

Xu, Z., et al., "Knocking down necleolin expression in gliomas inhibits tumor growth and induces cell cycle arrest," J Neurooncol, 2012, 108:59-67, 9 pgs.

Xu, Z., et al., "Orthotopic Patient-Derived Glioblastoma Xenografts in Mice," Methods Mol Biol, Ch. 14 in Dimitris G. Placantonakis (ed.), *Glioblastoma: Methods and Protocols*, Springer Science+Business Media, LLC, 2018, 1741:183-190, 8 pgs.

Yabroff, K.R., et al., "Patterns of care and survival for patients with glioblastoma multiforme diagnosed during 2006," Neuro-Oncol, 2012, 14(3):351-359, 9 pgs.

Yanagisawa, K., et al., "Proteomic patterns of tumour subsets in non-small-cell lung cancer," Lancet, 2003, 362(9382):433-439, 7 pgs.

Yao, F., et al., "Functional Data Analysis for Sparse Longitudinal Data," Journal of the American Statistical Association, 2005, 100(470):577-590, 14 pgs.

Yu, J., et al., "Biomarker Panel for Chronic Graft-Versus-Host Disease," J Clin Oncol, 2016, 34(22): 2583-2590, 10 pgs.

Yu, J., et al., "Comparison of Lung T2* During Free-Breathing at 1.5 T and 3.0 T with Ultrashort Echo Time Imaging," Magn Reson Med, 2011, 66(1):248-254, 7 pgs.

Yuan, M., et al., "A highly conserved cryptic epitope in the receptor-binding domains of SARS-CoV-2 and SARS-CoV," Science, 2020, 368:630-633, 4 pgs.

Yurek, D.M., et al., "Compacted DNA nanoparticle gene transfer of GDNF to the rat striatum enhances the survival of grafted fetal dopamine neurons," Cell Transplant., 2009, 18(10):1183-96, 15 pgs.

Yurek, D.M., et al., "DNA Nanoparticles: Detection of Long-term Transgene Activity in Brain Using Bioluminescence Imaging," Mol. Imaging, Apr. 26, 2011, 10(5):327-339, 12 pgs.

Yurek, D.M., et al., "Long-term transgene expression in the central nervous system using DNA nanoparticles," Mol. Ther., Apr. 2009, 17(4):641-50, 14 pgs.

Yurek, D., et al., "Intracerebral injections of DNA nanoparticles encoding for a therapeutic gene provide partial neuroprotection in an animal model of neurodegeneration," Nanomedicine: Nanotechnology, Biology, and Medicine, 2017, 13(7):2209-2217, 9 pgs.

Yurek, D.M., et al., "Age and lesion-induced increases of GDNF transgene expression in brain following intracerebral injections of DNA nanoparticles," Neuroscience, 2015, 284:500-512, 28 pgs.

Zarogoulidis, P., et al., "Suicide Gene Therapy for Cancer—Current Strategies," J Genet Syndr Gene Ther, 2013, 4, 29 pgs.

Zeitzer JM, et al., "Phenotyping Apathy in Individuals With Alzheimer Disease Using Functional Principal Component Analysis," Am J Geriatr Psychiatry, 2013, 21(4):391-397, 12 pgs.

Zemanick ET, et al., "Inflammation and Airway Microbiota During Cystic Fibrosis Pulmonary Exacerbations," PLoS One, 2013, 8(4):e62917, 13 pgs.

Zhang, J., et al., "Gene-Directed Enzyme Prodrug Therapy," AAPS J, 2015, 17(1):102-110, 9 pgs.

Zhang, X., et al., "CRISPR/Cas9 system: a powerful technology for in vivo and ex vivo gene therapy," Sci. China Life Sci, May 2017, 60(5):468-75, 8 pgs.

Zhou, H., et al., "Development of Human Serine Protease-Based Therapeutics Targeting Fn14 and Identification of Fn14 as a New Target Overexpressed in TNBC," Mol Cancer Ther, 2014, 13(11):2688-2705, 34 pgs.

Zhu, N., et al., "A Novel Coronavirus from Patients with Pneumonia in China, 2019," N Engl J Med, 2020, 382(8):727-733, 7 pgs.

Ziady, A.G., et al., "Current prospects for gene therapy of cystic fibrosis," Curr Opin Pharmacol, Oct. 2006, 6(5):515-21, 7 pgs.

Ziady, A.G., et al., "Functional evidence of CFTR gene transfer in nasal epithelium of cystic fibrosis mice in Vivo following luminal application of DNA complexes targeted to the serpin-enzyme complex receptor," Mol. Ther., Apr. 2002, 5(4):413-9, 7 pgs.

Ziady, A.G., et al., "Interaction with CREB binding protein modulates the activities of Nrf2 and NF-κB in cystic fibrosis airway epithelial cells," Am J Physiol Lung Cell Mol Physiol, 2012, 302(11):L1221-L1231, 11 pgs.

Ziady, A.G., et al., "Minimal Toxicity of Stabilized Compacted DNA Nanoparticles in the Murine Lung," Mol Ther, 2003, 8(6):948-956, 9 pgs.

Ziady, A.G., et al., "Non-viral gene transfer therapy for cystic fibrosis," Expert Opin Biol Ther, Jun. 2003, 3(3):449-58, 10 pgs.

Ziady, A.G., et al., "Protein Sequencing with Tandem Mass Spectrometry," Chapter 21, James Weifu Lee, et al., Eds. *Micro and Nano Technologies in Bioanalysis*, Methods Mol Biol, 2009, 544:325-341, 17 pgs.

Ziady, A.G., et al., "Proteomic Analyses of BALF Reveal Potential Biomarkers and Suggest Altered Lipid, Cyclic Nucleotide, and Iron Metabolism in Young CF Children Versus Disease Controls," Pediatr Pulmonol, 2013, 48(S36):277-278, 2013 Cystic Fibrosis Conference, Poster Session Abstract 204*, 2 pgs.

Ziady, A.G., et al., "Proteomic Analyses of Serum From CF Patients With Mild or Severe Disease Reveal the Differential Expression of Proteins That Regulate the Differentiation of Cartilage, Myeloid Leukocytes, and Intestinal Epithelia" Pediatr Pulmonol, 2014, 49(S38):288, 2014 Cystic Fibrosis Conference, Poster Session Abstract 206*, 1 pg.

Ziady, A.G., et al., "Redox balance in cystic fibrosis," Int J Biochem Cell Biol, 2014, 0:113-123, 27 pgs.

Ziady, A.G., et al., "Transfection of Airway Epithelium by Stable PEGylated Poly-L-lysine DNA Nanoparticles in Vivo," Mol Ther, 2003, 8(6):936-947, 12 pgs.

Zost, S.J., et al., "Potently neutralizing and protective human antibodies against SARS-CoV-2," Nature, 2020, 584(7821):443-449, 34 pgs.

Zwart, N.R., et al., "Graphical Programming Interface: A Development Environment for MRI Methods.," Magn Reson Med, 2015, 74(5):1449-1460, 12 pgs.

European Search Report, Extended, and Written Opinion dated Dec. 14, 2021 for Application No. EP 21180569.2, 11 pgs.

European Search Report, Supplementary, and Written Opinion dated May 15, 2023, for Application No. EP 20798040.0, 9 pgs.

International Search Report and Written Opinion dated Aug. 10, 2020 for Application No. PCT/US2020/030401, 10 pgs.

(56)　　　　　　References Cited

OTHER PUBLICATIONS

International Search Report and Written Opinion dated Dec. 30, 2021 for Application No. PCT/US2021/044587, 14 pgs.
International Search Report and Written Opinion dated Mar. 28, 2022 for Application No. PCT/US2021/062624, 16 pgs.
International Search Report and Written Opinion dated Jun. 7, 2022 for Application No. PCT/US2022/012561, 21 pgs.
International Search Report and Written Opinion dated Sep. 25, 2023 for Application No. PCT/US2023/020341, 21 pgs.
International Search Report and Written Opinion dated Sep. 25, 2023 for Application No. PCT/US2023/020337, 22 pgs.
Ndesendo, "Convection-Enhanced Delivery of Neurotherapeutics," In: V. Pillay and Y.E. Choonara, (Eds.), Advances in Neurotherapeutic Delivery Technologies, vol. 8, UK: OMICS International, 2015, https://doi.org/10.4172/978-1-63278-036-2-037, www.esciencecentral.org/ebooks, 3 pgs. (Bibliographic information only).
Abraham, D.J., (Ed), "Burger's Medicinal Chemistry and Drug Discovery", 6th ed., 818 pages.

\* cited by examiner

SERUM PROTEIN BIOMARKER PANEL FOR IDIOPATHIC PULMONARY FIBROSIS

CROSS-REFERENCE TO RELATED APPLICATIONS

This application claims priority to and benefit of International Application No. PCT/US20/54664, filed Oct. 8, 2020, entitled "Serum Protein Biomarker Panel for Idiopathic Pulmonary Fibrosis." which claims priority to and benefit of U.S. 62/912,228, filed on Oct. 8, 2019, entitled "Serum Protein Biomarker Panel that Predicts the Development and Resolution of Idiopathic Pulmonary Fibrosis" and U.S. 63/024,139 filed May 13 2020, entitled "Serum Protein Biomarker Panel the Predicts the Development and Resolution of Idiopathic Pulmonary Fibrosis, the contents of each are incorporated in their entirety for all purposes.

BACKGROUND

Lung fibrosis complicates many interstitial lung diseases (ILD) including systemic connective tissue diseases, childhood interstitial lung disease syndrome, and in response to many types of lung injury[1]. The natural history is often inconsistent and unpredictable, and in some specific disorders, such as idiopathic pulmonary fibrosis (IPF), inexorably progressive. This variability in the rate and severity of disease progression makes prognostication for individual patients challenging and creates significant barriers to efficient drug development. Validation of sensitive, reproducible, and objective biomarkers that accurately tracks disease, the fibrotic burden, and response to therapy would be of enormous benefit to clinicians as well as clinical researchers. The current standard of care for diagnosing and monitoring pulmonary fibrosis includes pulmonary function testing (PFTs), imaging by high-resolution computed tomography (HRCT), and surgical lung biopsy. PFTs, specifically spirometry, plethysmography and diffusion, measure lung volumes, airflow and gas uptake and are the widely used for their relative ease in performance, high safety profile, low cost and rapid results. However, PFTs are nonspecific for identifying the underlying pathology. Further, longitudinal monitoring with PFTs is imprecise due to the high variability of endpoints. For instance. Forced vital capacity (FVC), which is often the primary endpoint in IPF clinical trials, varies up to 11% week to week in normal subjects and up to 20% in patients with emphysema[2, 3]. With this variability, PFTs must be obtained and followed over extended periods to confidently follow disease course.

HRCT of the chest is routinely performed in patients with suspected fibrotic lung disease and the presence of typical clinical and radiographic features is sufficient to allow a confident diagnosis of fibrosis in more than 50% of suspected cases. While HRCT provides useful diagnostic information its prognostic value to track disease has several limitations including significant interobserver variability among radiologists in determining the extent of disease.[4] Another restraint is defining small changes in the fibrotic burden when performing serial studies, especially among individual patients with extensive disease at the time of diagnosis. Further, HRCT has not been shown to reliably identify treatment failure early in trials of therapy.[5]

Surgical lung biopsy is the gold standard for diagnosis pulmonary fibrosis. However, the risk of performing a lung biopsy may be impracticable especially in patients with advanced disease or comorbidities. With an in-hospital mortality of 4.6%, surgical lung biopsies cannot be performed longitudinally to monitor fibrosis progression.[6]

Taken as a whole, currently there are no rapid predictors of disease progression for pulmonary fibrosis disorders. The discovery and development of pulmonary fibrosis-specific biomarkers for use as diagnostic adjuncts or measures of disease activity or treatment response remains a critical unmet need. Newly discovered biomarkers of human disease may reflect disease pathogenesis, change with intervention, and/or offer diagnostic or prognostic value beyond current measures.[7]

The foregoing disclosure addresses one or more of the aforementioned needs in the art.

BRIEF SUMMARY

The instant disclosure relates to methods for assessing pulmonary fibrosis disorder disease status in an individual in need thereof. One aspect of the disclosed methods may comprise: detecting a level of one or more biomarkers in a biological sample obtained from an individual, comparing the level of the one or more biomarkers to that of a control value corresponding to the one or more biomarkers, characterizing the disease status in the individual based on the level of the one or more biomarkers as compared to that of a relevant control value; and administering a treatment to said individual based on the assessment of the one or more biomarker levels.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION

Definitions

Figure 1:
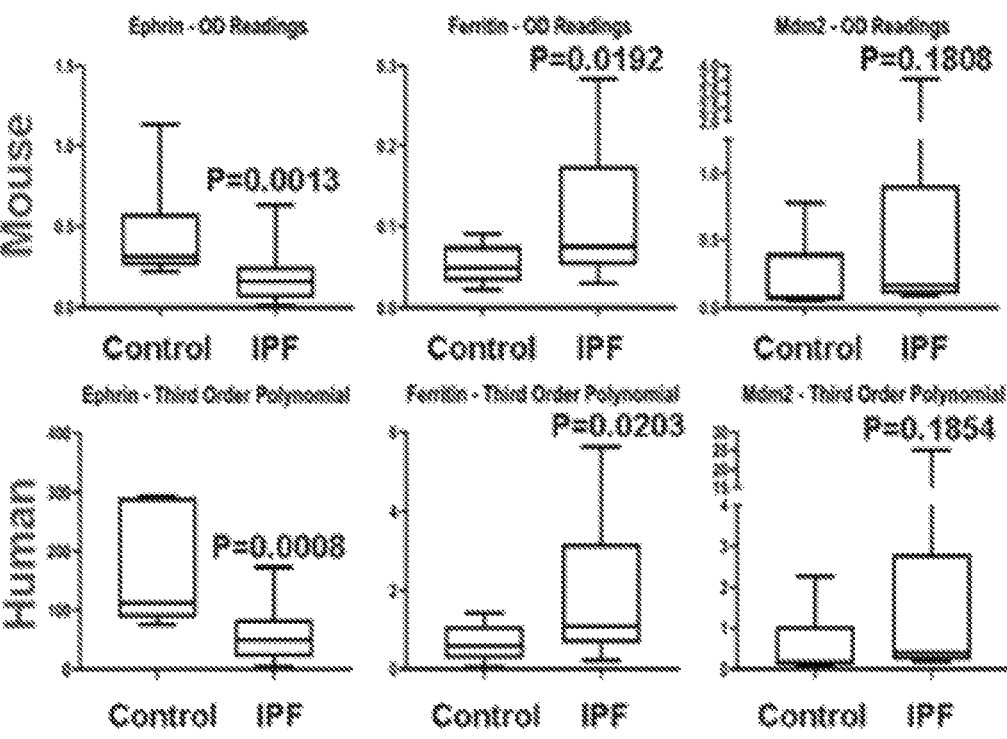
FIG. 1. ELISA confirmation of markers of IPF identified in model mouse plasma by MS proteomics. Protein markers in plasma that significantly changed in the IPPF condition were identified by discovery proteomics and validated by ELISA in mouse and human plasma. Conditions were compared by ANOVA with Dunnett's multiple comparisons correction.

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, or up to 10%, or up to 5%, or up to 1% of a given value. Alternatively, particularly with respect to biological systems or processes, the term may mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

As used herein, the term "measuring" refers to methods which include one or more of detecting the presence or absence of a biomarker in a sample, quantifying the amount of marker(s) in the sample, with or without reference to a control value. Measuring/analyzing/quantifying the level of a biomarker provided herein, may be performed using methods know in the art. For example, methods to determine the level of a biomarker include, but are not limited to, PCR, microarray assays, immunoblots, northern blots, ELISA, fluorescence-based methods (immunofluorescence, FACS), mass spectrometry, and the like.

As used herein, the term "expression" refers to the transcription and stable accumulation of sense (mRNA) or antisense RNA derived from a nucleic acid fragment or fragments. Expression also refers to the translation of mRNA into a polypeptide. Biomarker expression may be one or more of tissue-specific, global, or systemic.

As used herein, "biological sample" may refer to any biological sample from an individual, and may include, for example, blood, serum, plasma, sperm, urine, mucous, tissue biopsy, organ biopsy, synovial fluid, urine, bile fluid, cerebrospinal fluid, saliva, mucosal secretion, effusion, sweat and combinations thereof. In some aspects, the biological sample may be diluted with a suitable diluent before detecting the level of a biomarker in the sample.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Determining the expression of a disclosed biomarker may include assessing gene product or protein abundance. Protein abundance reflects gene expression profiles, which may be determined, by methods known in the art, such as, but not limited to Western blot analysis, RIA, ELISA, HPLC, functional assays, such as enzymatic assays, as applicable, and others. An expression profile may be determined by a change in mRNA levels, surface expression, secretion, or other partitioning of a polypeptide.

"Solid support" refers to a solid material which can be derivatized with, or otherwise attached to, a capture reagent. Exemplary solid supports include probes, microtiter plates and chromatographic resins.

As used herein, "changed expression" or "change in level" or "changed level" refer to a change in the level or amount of a biomarker relative to the level or activity of the biomarker in a standard. A change in level may refer to between a 10 to about a 1000% change in biomarker levels in a biological sample. The change in a biological maker level taken from an individual may be 1-10%, 11-20%, 21-30%, 31-40%, 41-50%, 51-60%, 61-70%, 71-80%, 81-90%, 91-150%, 151-1000% elevated or reduced as compared to the level(s) of that biomarkertaken from a normal subject (standard).

In one aspect, disclosed herein are methods for assessing pulmonary fibrosis disorder disease status in an individual in need thereof. The method may comprise
    a. detecting a level of one or more biomarkers in a biological sample obtained from said individual;
    b. comparing the level to that of a control value;
    c. characterizing the disease status in said individual based on the level detected in the individual as compared to that of a control value; and
    d. administering a treatment to said individual, wherein the treatment selection is based on the characterization step.

In one aspect, the biomarker may be selected from one or more of selected from Ephrin B2, Epidermal Growth Factor, Ferritin-heavy chain, Apotransferrin, Phosphoinositide 3-kinase, Mdm2-binding protein isoform X3, Tubulin polyglutamylase TTLL13 isoform X7, Heparin sulfate glucosamine 3-O-sulfotransferase 2, pregnancy zone protein, serotransferrin, alpha-2-macroglobulin, immunoglobulin lambda-like polypeptide 5, ceruloplasmin, alpha-1-antitrypsin precursor, complement C3 preproprotein, coiled-coil domain-containing protein 144A, cytochrome P450 3A43, myosin phosphatase Rho-interacting protein, collagen alpha-6(IV) chain protein FAM110A, DNA polymerase epsilon catalytic subunit A, semaphorin-5B, ephrin type-B receptor 1, zinc finger protein 532, tyrosine—tRNA ligase (cytoplasmic), mismatch repair endonuclease PMS2, cadherin EGF LAG seven-pass G-type receptor, cytoskeleton-associated protein 2, tyrosine—tRNA ligase (cytoplasmic), zinc finger protein 618, cytoskeleton-associated protein 2, alpha-2-macroglobulin, serine/threonine-protein kinase OSR1, collagen alpha-1(XII) chain, zinc finger ZZ-type and EF-hand domain-containing protein 1, iporin, phospholipid-transporting ATPase IG, collagen alpha-6(IV) chain, spatacsin, short stature homeobox protein 2, collagen alpha-1(XII) chain, ubiquitin carboxyl-terminal hydrolase 28, phospholipid-transporting ATPase IG, cyclin-dependent kinase 13, A-kinase anchor protein 9, zinc finger protein 417, sorting nexin-13, hemoglobin subunit beta, hemoglobin subunit delta, hemoglobin subunit alpha, cytochrome P450 3A4 isoform, filamin-C, apolipoprotein A-IV, nebulin, SAA2-SAA2 protein precursor, plasminogen isoform 1 precursor, ATPase family AAA domain-containing protein 5, DNA damage-induced apoptosis suppressor protein, E3 ubiquitin-protein ligase Midline-1, mitogen-activated protein kinase kinase kinase 1, mucin-16, probable E3 ubiquitin-protein ligase HECTD4, protein RRP5 homolog, retrotransposon Gag-like protein 9, serine/threonine-protein phosphatase 2A regulatory subunit B" subunit gamma, and uncharacterized protein C12orf42.

In one aspect, the biomarker may be selected from one or more of Ephrin B2, Epidermal Growth Factor, Ferritin-heavy chain, Apotransferrin, Phosphoinositide 3-kinase, Mdm2-binding protein isoform X3, Tubulin polyglutamy-lase TTLL13 isoform X7, Heparin sulfate glucosamine 3-O-sulfotransferase 2.

In one aspect, the characterization of the disclosed method may be identifying an individual as having improved disease, progressing disease, or a plateau in disease.

In one aspect, an alteration or change in a biomarker level compared to a control level indicates one or both of the presence of disease or progression of disease.

In one aspect, the method may comprise a second comparison, wherein the second comparison is carried out following administration of a treatment. In this aspect, a return, or a trend to a return, to a biomarker level to that of a control value indicates an improvement in disease. In other words, following administration of a treatment, a second comparison in which an aberrant or abnormal biomarker returns to a normal level (a normalization of the biomarker) indicates that the treatment is effective. In such cases, the treatment may be continued until complete normalization. In further aspects, if a normalization or trend towards normalization does not occur, then an increased dose or frequency of the treatment may be administered, or alternatively, an alternative treatment may be used.

In one aspect, the pulmonary fibrosis disease may be selected from progressive pulmonary fibrosis, interstitial lung disease (ILD), and idiopathic pulmonary fibrosis (IPF).

In one aspect, the treatment may be any treatment known to be efficacious for a pulmonary fibrosis disease. In certain aspects, for example, the treatment may be selected from one or more of a PI3K pathway inhibitor, an EGF pathway inhibitor, pirfenidone (a medication used for the treatment of idiopathic pulmonary fibrosis that works by reducing lung fibrosis through downregulation of the production of growth factors and procollagens I and II), nintendanib (sold under the brand names Ofev and Vargatef, an oral medication used for the treatment of idiopathic pulmonary fibrosis and for some types of non-small-cell lung cancer), and combinations thereof). Exemplary EGF pathway inhibitors include erlotinib, cetuximab, panitumumab, gefitinib, erlotinib, lapatinib, canertinib, and combinations thereof. Exemplary PI3K pathway inhibitors include alpelisib, taselisib, idelalisib, and combinations thereof.

In one aspect, the individual may be one having, or at high-risk of having or of developing idiopathic pulmonary fibrosis (IPF), wherein the methods are used to determine disease status. Disease status may include having a trajectory of improvement, disease progression, or disease stagnation, particularly with respect to IPF status. In one aspect, the high-risk individual is one having one or more predispositions selected from a familial history of IPF, age of 60 years or greater, and a history of chronic smoking.

In one aspect, a method for monitoring idiopathic pulmonary fibrosis (IPF) progression in an individual in need thereof is disclosed. In this aspect, the method may comprise assaying one or more of the aforementioned biomarkers.

In one aspect, a method for testing a potential therapeutic in an individual having idiopathic pulmonary fibrosis (IPF) is disclosed, in which the method may comprise assaying one or more biomarkers at a time point selected from one or more of before, during, or after administration of a potential therapeutic agent, wherein a normalization of a level of a biomarker following treatment indicates that the potential therapeutic has efficacy in treating IPF. The methods may be further used to assist in dosage, including amount and frequency of the dose, wherein the methods may be used to determine whether an increased or more frequent dosage contributes to an improved or enhanced normalization of an abnormal biomarker level. Yet further, using the methods, it may be determined that a lesser dosage or frequency may be used to obtain a similarly efficacious result of normalizing biomarkers (and in turn, disease status or progression).

In one aspect, a method of diagnosing and treating a pulmonary disease as disclosed herein, for example, idiopathic pulmonary fibrosis (IPF) in an individual in need thereof is disclosed. In this aspect, the method may comprise
   a) establishing, using a computing system, a model for characterizing the disease state of an individual having or likely to have a pulmonary disease, by using expression level data of one or more of the disclosed biomarkers;
   b) contacting a biological sample from said individual with at least one detection agent capable of specifically binding to said one or more biomarkers;
   c) acquiring an expression level from said one or more biomarkers measured from said biological sample;
   d) characterizing said individual as one or more of "likely to have a lung disease," "having stable lung disease," "having progressive lung disease," or "having improving lung disease;" and
   e) optionally, administering a therapy to said individual based on said characterization.

Detection Methods

The disclosed methods may use any methods known in the art for detection of a biomarker. The methods may include the diagnosis, prognosis, stratification and/or monitoring of disease in a human subject, and may, in certain aspects comprise a) detecting a level of one or more biomarker proteins in a biological sample obtained from the human subject, wherein a higher or lower level of the one or more biomarker protein in the biological sample from the human subject compared to a reference value (such as that of a control subject that does not have the disease state of interest) is indicative of the state of the disease, for example, a pulmonary fibrosis disorder, more particularly, in certain aspects, IPF. The state of a pulmonary disorder that may be determined using the methods may include the propensity or likelihood of developing the disorder, the progression of the disorder, or the resolution of the disorder, with or without a therapeutic intervention.

The disclosed methods may employ a variety of different methods for detecting one or more biomarkers and/or quantifying or determining a relative level of one or more biomarkers. The methods may include protein level measurements, DNA measurements, or RNA measurements. In certain exemplary aspects, the one or more biomarkers may be detected as proteins, which may be detected using one or more antibodies specific for the biomarker protein as is described herein, for example, one or more of western blot, ELISA, Proximity Extension Assay, or mass-spectrometrically, though it is expressly noted that any method sufficient to distinguish levels of the aforementioned one or more biomarkers, whether as protein or mRNA, or any other measure of gene expression, may be used with the disclosed methods and the examples herein are not intended to limit the scope of the invention.

Methods for capturing, analyzing, quantifying, etc., biomarkers are known in the art and may be used in conjunction with the disclosed methods. For example, in one aspect, one or more of the disclosed biomarkers may be captured with capture reagents immobilized to a solid support, such as a biochip or other substrate suitable for such capture, and may include, for example, a glass or plastic in the form of, e.g., a microtiter plate, a stick, a bead, or a microbead. Once captured on a substrate, the marker or markers in a sample may be assayed for presence and/or quantity/abundance. In one aspect, one or more of the disclosed biomarkers may be detected and/or measured by a variety of detection methods including for example, gas phase ion spectrometry methods, optical methods, electrochemical methods, atomic force microscopy and radio frequency methods.

In one aspect, a sample obtained from an individual may be prepared to enhance detectability of one or more biomarkers therein. For example, a blood serum sample may be fractionated using methods known in the art. Examples in include Cibacron blue agarose chromatography and single stranded DNA affinity chromatography, anion exchange chromatography, affinity chromatography (e.g., with antibodies) and the like. Such fractionation may be carried out prior to detection of the biomarker. The method of fractionation may depend on the type of detection method used. Methods that enriches for the protein of interest can be used. Sample preparations, such as pre-fractionation protocols, are optional and may not be necessary to enhance detectability of markers depending on the methods of detection used. In one aspect, biomarkers in a sample may be separated by high-resolution electrophoresis, e.g., one or two-dimensional gel electrophoresis. A fraction containing a marker can be isolated and further analyzed by gas phase ion spectrometry. In another embodiment, two-dimensional gel electrophoresis is used to generate two-dimensional array of spots of biomarkers, including one or more markers.

In one aspect, an immunoassay may be used to detect and analyze a biomarker in a sample. In this aspect, the method may comprise (a) providing an antibody that specifically binds to a marker; (b) contacting a sample with the antibody; and (c) detecting the presence of a complex of the antibody bound to the marker in the sample. For example, an exemplary immunoassay employs an antibody to specifically bind an antigen (e.g., a marker), and uses the specific binding properties of a particular antibody to isolate, target, and/or quantify the antigen. The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. For example, polyclonal antibodies can be selected to obtain only those polyclonal antibodies that are specifically immunoreactive with that marker and not with other proteins, except for polymorphic variants and alleles of the marker. This selection may be achieved by subtracting out antibodies that cross-react with the marker molecules from other species.

In one aspect, the method of detection may employ a labeled detection reagent. For example, the detection reagent may be, e.g., a first or second antibody labeled with a detectable label. Exemplary detectable labels include magnetic beads (e.g., DYNABEADS™), fluorescent dyes, radiolabels, enzymes (e.g., horse radish peroxidase, alkaline phosphatase and others commonly used in an ELISA), and colorimetric labels such as colloidal gold or colored glass or plastic beads. Alternatively, the marker in the sample can be detected using an indirect assay, wherein, for example, a second, labeled antibody may used to detect bound marker-specific antibody, and/or in a competition or inhibition assay wherein, for example, a monoclonal antibody which binds to a distinct epitope of the marker may incubated simultaneously with the mixture.

Exemplary methods for measuring the amount of, or presence of, one or more biomarkers include detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Electrochemical methods include voltametry and amperometry methods. Radio frequency methods include multipolar resonance spectroscopy. Methods for performing these assays are known in the art and may include an enzyme immune assay (EIA) such as enzyme-linked immunosorbent assay (ELISA), a radioimmune assay (RIA), a Western blot assay, or a slot blot assay.

In one aspect, the method may employ an incubation step or a washing step. For example, incubation steps may vary from about 5 seconds to several hours, or from about 5 minutes to about 24 hours. The incubation time will depend upon the assay format, marker, volume of solution, concentrations, and the like. The methods may be carried out at ambient temperature, or may be conducted over a range of temperatures, such as 10° C. to 40° C.

In one aspect, the methods employ an immunoassays to determine presence or absence of a marker in a sample, as well as the quantity of a marker in a sample, in which the amount of an antibody-marker complex may be determined by comparing to a standard. A standard can be, e.g., a known compound or another protein known to be present in a sample which would be expected to remain unchanged in the presence of the disease state being evaluated. The test amount of marker need not be measured in absolute units, as long as the unit of measurement can be compared to a control.

In one aspect, the biomarker may be detected, and biomarker data may be generated, wherein the data may then be analyzed by a computer software program. The software may comprise code that converts signal from the mass spectrometer into computer readable form, and may include code that applies an algorithm to the analysis of the signal to determine whether the signal represents a "peak" in the signal corresponding to one or more markers as disclosed herein. The software may also include code that executes an algorithm that compares signal from a test sample to a typical signal characteristic of a "normal" sample obtained from an individual known to not have a disease state contemplated herein, and determines the closeness of fit between the two signals. The software also can include code indicating which the test sample is closest to, thereby providing a probable diagnosis, trajectory, and/or disease outcome.

Kits

In one embodiment, provided herein are kits comprising reagents for detecting one or more biomarker levels, wherein the reagents may include antibodies and/or nucleic acids, which may hybridize to the mRNA or protein of the biomarker(s) of a biological sample. Reagents may be labelled for subsequent detection, wherein the detection allows for measurement, whether absolute or relative, of the biomarker level. In other aspect, the kit may include instructions for detecting the label qualitatively or quantitatively. In another aspects, disclosed are kits for using the disclosed biomarkers which further include assays and analytical tools for the assays, such as one or more of reagents, standards and instructions for analyzing the expression level of one or more biomarkers in a biological sample. The kit may comprise, in certain aspects, a buffering agent, a preservative, or a protein stabilizing agent, an enzyme, or a substrate. The substrate may be a means of detecting a label, or the expressed biomarker protein product itself, which may further include mRNA associated with the biomarker protein. In one aspect, the kit may comprise reagents that may be necessary for detection of nucleic acids, amino acids or hybridization signals for nucleic acids.

In one aspect, the results obtained may be compared to a standard, which, may, for example, comprise a series of standards. The standard(s) may be used in the kits for quantification of differential levels of the biomarker or differential expression. In one aspect, the standard may comprise antibodies for detecting a standard biomarker. In one aspect, the standard may comprise nucleic acids when the kit is used for the determination of nucleic acid profile, or in another aspect the standard is a protein when the kit is used for the determination of expressed protein profile. The kit may be adapted for high-throughput screening, and comprise a microarray. In certain aspects, the kit may comprise a microarray, which may comprise cRNA of the genes indicated, and others. In one aspect, the kit may comprise one or more of standard oligonucleotide probes, PCR reagents and detectable labels. The kit further may comprise a positive and negative control, wherein said standards can be assayed and compared to the test sample. Kits that include one or more reaction vessels that have aliquots of some or all of the reaction components of the invention in them may be provided. Aliquots can be in liquid or dried form. Reaction vessels can include sample processing cartridges or other vessels that allow for the containment, processing and/or amplification of samples in the same vessel.

Examples

The following non-limiting examples are provided to further illustrate embodiments of the invention disclosed herein. It should be appreciated by those of skill in the art that the techniques disclosed in the examples that follow represent approaches that have been found to function well in the practice of the invention, and thus may be considered to constitute examples of modes for its practice. However, those of skill in the art should, in light of the present disclosure, appreciate that many changes may be made in the specific embodiments that are disclosed and still obtain a like or similar result without departing from the spirit and scope of the invention.

The instant disclosure relates to methods for the characterization and/or treatment of pulmonary disease and fibrosis using biomarkers of pulmonary injury or early predictors of interstitial lung disease. Further disclosed are improved tools to study pulmonary fibrosis and evaluate therapeutics.

To guide in the selection of candidate plasma biomarkers of pulmonary fibrosis, Applicant studied a transgenic mouse model of progressive pulmonary fibrosis where fibrosis is induced by overexpressing transforming growth factor-alpha (TGFα). Mice in this model develop histological, biochemical and physiological changes similar to those seen in human fibrotic disease including gene expression profiles, migrating fibrotic lesions, severe restrictive changes in lung mechanics, cachexia and ultimately death from a progressive fibrotic burden.[8] Despite the severe and progressive nature of the fibrosis, these lesions are partially reversible when the transgene or downstream signaling pathways are extinguished.[9] This unique feature of the model allows for identification of biomarkers of fibrosis progression and resolution.

In preliminary data, Applicant performed mass spectrometry on mouse plasma from TGFα mice and identified candidate proteins that were altered during the progression of fibrosis and returned to baseline during regression. Through our collaboration with the University of Michigan we next obtained plasma from a longitudinal cohort of carefully phenotyped patients with IPF, The COMET Study. The COMET study was a multi-center, observational cohort of highly characterized IPF patients followed prospectively up to 80 weeks. All subjects underwent baseline assessment, including demographics, patient-reported descriptors, PFTs and plasma samples which were prospectively repeated at 16-week intervals. Within this cohort are patients whose disease progressed during the 80-week period and patients who were stable. These samples thus represented a highly unique and valuable resource for identifying plasma protein changes associated with physiologic and clinical changes in IPF disease progression. To determine potential relevance of murine plasma candidates with human disease, Applicant identified Ephrin-B2, Mdm2-binding protein and ferritin heavy chain, all proteins which have been shown to mediate fibrogenesis in IPF cell lines or experimental models of fibrosis in the liver and kidney[10-11]. Applicant then performed ELISA for Ephrin, Mdm2 and ferritin on IPF plasma samples and normal human controls and compared with TGFα mice. ELISA results in the IPF group were altered from controls mirroring differences in the fibrotic mouse model (FIG. 1).

Figure 2:
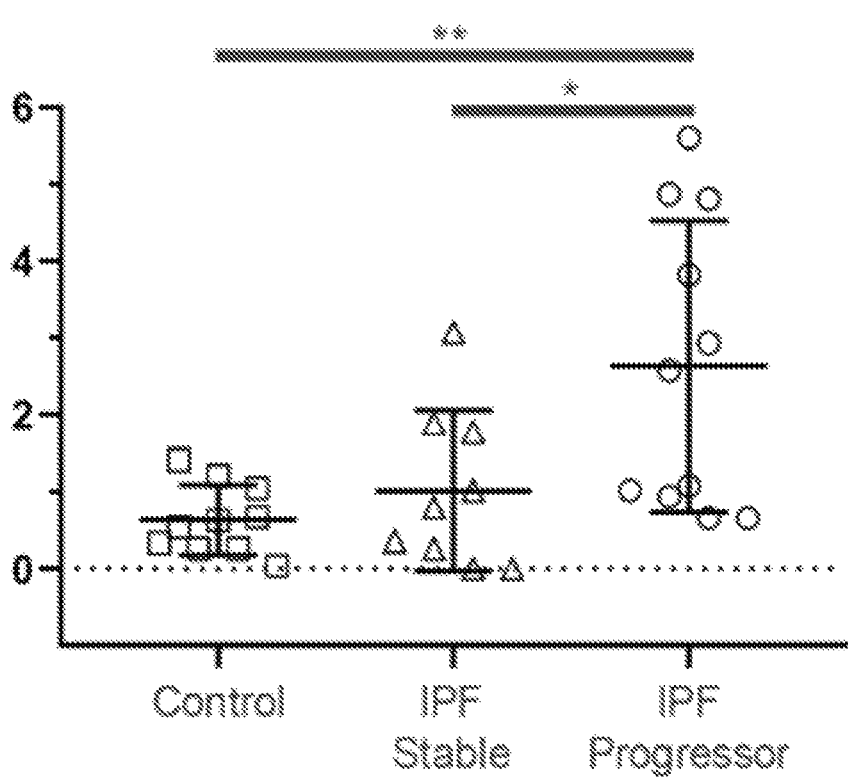
FIG. 2. ELISA confirmation of Ferritin identified by MS proteomics as a marker of IPF resolution. Conditions were compared by ANOVA with Dunnett's multiple comparisons correction *$p<0.05$; **$p<0.01$.

Among the samples analyzed by ELISA were subgroups of patients whose fibrotic disease was stable or progressed. When comparing ferritin levels among these subgroups, those individuals whose disease advanced had higher levels compared with patients whose disease remained stable (FIG. 2). Taken together, this preliminary data demonstrates a strong correlation in altered plasma proteins identified by mass spectrometry in the TGFα mouse model with HT plasma samples. These findings demonstrate the feasibility that a murine model combined with human samples can identify specific plasma markers of pulmonary fibrosis progression.

Applicant then performed an unbiased mass spectrometry analysis on the plasma of 35 COMET Study patients and 17 age-matched controls. Using the data from this proteomic analysis, Applicant identified additional candidate proteins associated with pulmonary fibrosis (Table 1). Pathway analysis of these biomarkers revealed dysfunction in a number of pathways that can be modulated with FDA approved drug therapeutics (Table 2).

Exemplary inhibitors of the PI3K pathway include alpelisib, taselisib, and idelalisib. Alpelisib (BYL719; Novartis Pharmaceuticals, Basel, Switzerland) is the first oral PI3Ki to selectively target the class I p110α-isoform (IC50=4.6 nM). A phase I trial (NCT01219699) included patients with PIK3CA-altered advanced solid tumors and showed sensitivity to alpelisib monotherapy. See, e.g. LoRusso P M. Inhibition of the PI3K/AKT/mTOR Pathway in Solid Tumors. J Clin Oncol. 2016 Nov. 1; 34(31):3803-3815. doi: 10.1200/JCO.2014.59.0018. Epub 2016 Sep. 30. PMID: 27621407; PMCID: PMC6366304. Taselisib (GDC-0032, Genentech, San Francisco, CA) is an oral class I PI3Ki, sometimes referred as β-sparing, as it exhibits equipotent inhibition of p110α, p110-γ and p110-δ, but inhibits p110β with 30-fold lower potency. Idelalisib (Zydelig tablets; Gilead Sciences, Inc.) described chemically as 5-fluoro-3-phenyl-2-[(1S)-1-(9H-purin-6-yl-amino)propyl] quinazolin-4(3H)-one, is a lipid kinase inhibitor of the class I phophatidylinositol-3 kinase p110-δ (PI3K-δ). See, e.g., Clin Cancer Res Apr. 1, 2015 (21) (7) 1525-1529; DOI: 10.1158/1078-0432.CCR-14-2522

Exemplary inhibitors of the EGF pathway include erlotinib, cetuximab, panitumumab, gefitinib, erlotinib, lapatinib, and canertinib. See, for example, Seshacharyulu P, Ponnusamy M P, Haridas D, Jain M, Ganti A K, Batra S K. Targeting the EGFR signaling pathway in cancer therapy. Expert Opin Ther Targets. 2012 January; 16(1):15-31. doi: 10.1517/14728222.2011.648617. Epub 2012 Jan. 12. PMID: 22239438; PMCID: PMC3291787, describing such agents. Gifitinib (ZD1839/Iressa): Gefitinib is an anilinoquinazoline derived EGFR tryrosine kinase inhibitor and was first characterized in the year 1996. It is an orally active low-molecular-weight EGFR inhibitor with selective tyrosine kinase activity but does not inhibit serine-threonine kinase activity. Gefitinib has a 200-fold greater affinity for EGFR relative to the other ErbB family members. Erlotinib (also referred to as OSI-774, or Tarceva, Erlotinib hydrochloride is another FDA-approved low molecular weight molecule similar to gefitinib, available in the form of an orally potent and selectively reversible inhibitor of EGFR tyrosine kinase). Gefitinib (ZD1839/Iressa): Gefitinib is an anilinoquinazoline derived EGFR tryrosine kinase inhibitor and was first characterized in the year 1996. It is an orally active low-molecular-weight EGFR inhibitor with selective tyrosine kinase activity but does not inhibit serine-threonine kinase activity. Lapatinib (GW-572016): Lapatinib is an orally active, reversible and specific RTK inhibitor of both EGFR and HER2 as well it was also found to exhibit activity against an found to have activity against AKT overexpressing human tumor xenografts. Due to its nonselective nature of EGFR inhibition, it accounts for a broader spectrum of anti-tumor activity with improved efficacy. Canertinib (CI-1033): Canertinib is a 3-chloro 4-fluoro 4-anilinoquinazoline compound. It is an orally active low-molecular-weight irreversible pan-EGFR family TKI.

TABLE 2

Targetable pathways enriched by markers.

| Pathway | FDR-corrected P value |
|---|---|
| P13K signaling and response to cAMP | 3.918e−14 |
| Iron transport and homeostasis | 1.841e−13 |
| Platelet activation | 2.039e−11 |
| Blood coagulation | 1.368e−10 |
| Cellular adhesion and integrin priming | 4.168e−10 |
| Cellular proliferation and apoptosis | 4.0583−7 |
| Interleukin 10 anti-inflammatory signaling | 1.853e−5 |

TABLE 3

Additional IPF Biomarkers. The category of "IPF v Non IPF" are those proteins present in IPF and controls but more different in IPF than non-IPF controls. "Present only in IPF" is proteins only seen in IPF and not in controls while "Missing in IPF" is the corollary.

idiopathic pulmonary fibrosis (IPF) v Non idiopathic pulmonary fibrosis (IPF)

pregnancy zone protein
serotransferrin
alpha-2-macroglobulin
immunoglobulin lambda-like polypeptide 5
ceruloplasmin
alpha-1-antitrypsin precursor
complement C3 preproprotein
coiled-coil domain-containing protein 144A
cytochrome P450 3A43
myosin phosphatase Rho-interacting protein
collagen alpha-6(IV) chain
protein FAM110A
DNA polymerase epsilon catalytic subunit A
semaphorin-5B
ephrin type-B receptor 1
zinc finger protein 532
tyrosine--tRNA ligase, cytoplasmic
mismatch repair endonuclease PMS2

TABLE 1

Plasma proteins changed in human IPF samples and/or mouse TGF-alpha fibrosis model

| Marker | Function | Association with Fibrosis |
|---|---|---|
| Ephrin B2 | Cell surface transmembrane ligand for Ephrin receptors. Plays key role in cell migration | Pro-fibrotic role of Ephrin B2 in cardiac and liver |
| Epidermal Growth Factor | Ligand that binds EGFR. Stimulates the growth of various epidermal and epithelial tissues | Significantly differs in IPF |
| Ferritin-heavy chain | Stores iron in a soluble, non-toxic, readily available form | Elevated serum ferritin is an independent predictor of histologic severity and advanced liver fibrosis |
| Apotransferrin | Binds iron. Facilitates iron transport | Marker of liver fibrosis |
| Phosphoinositide 3-kinase | Regulates cell proliferation and migration | Involved in MTOR regulation in fibrosis |
| Mdm2-binding protein isoform X3 | Inhibits cell migration | Significantly Changed in epithelial cells from patients with IPF |
| Tubulin polyglutamylase TTLL13 isoform X7 | Modifies alpha-tubulin. Involved in elongation of the polyglutamylation reaction | Involved in lung remodeling |
| Heparin sulfate glucosamine 3-O-sulfotransferase 2 | Utilizes 3'-phospho-5'adenylyl sulfate (PAPS) to catalyze the transfer of a sulfo group | Significantly changed in kidney fibrosis |

TABLE 3-continued

Additional IPF Biomarkers. The category of "IPF v Non IPF"
are those proteins present in IPF and controls but more different
in IPF than non-IPF controls. "Present only in IPF"
is proteins only seen in IPF and not in controls while "Missing
in IPF" is the corollary.

cadherin EGF LAG seven-pass G-type receptor
cytoskeleton-associated protein 2
tyrosine-tRNA ligase, cytoplasmic
zinc finger protein 618
cytoskeleton-associated protein 2
alpha-2-macroglobulin
serine/threonine-protein kinase OSR1
collagen alpha-1(XII) chain
zinc finger ZZ-type and EF-hand domain-containing protein 1
iporin
phospholipid-transporting ATPase IG
collagen alpha-6(IV) chain
Spatacsin
short stature homeobox protein 2
collagen alpha-1(XII) chain
ubiquitin carboxyl-terminal hydrolase 28
phospholipid-transporting ATPase IG
cyclin-dependent kinase 13
A-kinase anchor protein 9
zinc finger protein 417
sorting nexin-13
Present only in idiopathic pulmonary fibrosis (IPF):

hemoglobin subunit beta
hemoglobin subunit delta
hemoglobin subunit alpha
cytochrome P450 3A4 isoform
filamin-C
apolipoprotein A-IV
nebulin
SAA2-SAA2 protein precursor
plasminogen isoform 1 precursor
Missing in idiopathic pulmonary fibrosis (IPF):

ATPase family AAA domain-containing protein 5
DNA damage-induced apoptosis suppressor protein
E3 ubiquitin-protein ligase Midline-1
mitogen-activated protein kinase kinase kinase kinase 1
mucin-16
probable E3 ubiquitin-protein ligase HECTD4
protein RRP5 homolog
retrotransposon Gag-like protein 9
serine/threonine-protein phosphatase 2A regulatory subunit
B'' subunit gamma
ubiquitin carboxyl-terminal hydrolase 28
uncharacterized protein C12orf42

The underlying hypothesis of Applicant's efforts is there are specific proteins which are altered in the plasma of patients with progressive pulmonary fibrotic disease which can be detected by mass spectrometry. A unique plasma biomarker profile may be useful to clinicians and clinical researchers to help diagnosis fibrotic disease, monitor disease progression and investigate the efficacy of antifibrotic therapies. The concept of measuring plasma protein biomarker panels to detect or monitor disease is already in practice in multiple processes with high accuracy[13]. However, there are currently no commercial tests blood tests which can monitor pulmonary fibrosis.

Combining Applicant's previous identification of plasma proteins from the murine TGF model with larger-scale mass spectrometry analysis of IPF and control samples, Applicant has now identified candidate proteins which may be used to discriminate pulmonary fibrosis from healthy lung and/or to evaluate progression of disease. Progression of disease can be defined as any of the following: death, acute exacerbation of IPF, lung transplant, or relative change in FVC of 10% or DLCO of 15%. Temporal association of blood draws and clinical assessment allows comparison of the timing of changes in plasma proteins with disease course. In sum, the identified markers of pulmonary fibrosis disease progression may be obtained rapidly, noninvasively and directly reflect the underlying pathophysiology of the disease process.

The identified biomarkers may be used for one or more of the following:

Monitoring disease (e.g., IPF) progression: Pulmonary fibrotic diseases including IPF will often intermittently progress. A sensitive plasma profile may provide improved guidance for clinical management decisions. For instance, a plasma profile indicating alterations in fibrotic proteins would indicate early progression of disease which may not be detected immediately by PFT or HRCT. Such findings may then be use for more rapid changes in initiation or adjustment of medications or earlier referral for lung transplantation. Alternatively, if a plasma profile is unaltered, these findings would suggest disease stability and no changes in management.

Early disease (e.g., IPF) diagnosis: A plasma profile specific for the development or progression of fibrotic disease would be highly valuable for early discrimination of pulmonary fibrosis in various disease states such as interstitial lung diseases (ILD). There are over 200 ILD, many of which have the potential to develop fibrosis as a complicating feature. A blood proteome signature specific for fibrosis would be an important diagnostic adjunct by allowing the clinician to determine if pulmonary fibrosis is a component of the ILD. Results from this assay would be useful in assisting with the determination if pulmonary fibrosis is present or developing and guiding in the management of antifibrotic therapy.

Companion diagnostic: Plasma biomarkers of fibrosis progression would provide a valuable tool for clinical researchers. Progression of fibrosis is often an insidious process developing over several years and current markers of progression are indirect and insensitive. Consequently, clinical trials often need to have large sample sizes and be of long duration adding significant cost and potentially reducing the number of promising agents which could be entered into early clinical trials. This decade will likely introduce several novel and promising antifibrotic compounds for the treatment of pulmonary fibrosis. Providing clinical researchers with sensitive plasma markers correlated with fibrosis progression will potentially enable more novel compounds to enter clinical trials by reducing the number of patients, length of time and subsequent cost currently needed to assess efficacy.

REFERENCES

1. Hardie W D, Glasser S W, Hagood J S. Emerging concepts in the pathogenesis of lung fibrosis. 2009; 175(1):3-16.
2. Miller M R, Hankinson J, Brusasco V, et al. Standardisation of spirometry. 2005; 26(2):319-338.
3. Pellegrino R, Viegi G, Brusasco V, et al. Interpretative strategies for lung function tests. 2005; 26(5):948-968.
4. Lynch D A, Godwin J D, Safrin S, et al. High-resolution computed tomography in idiopathic pulmonary fibrosis: diagnosis and prognosis. 2005; 172(4):488-493.
5. Wu X, Kim G H, Salisbury M L, et al. Computed Tomographic Biomarkers in Idiopathic Pulmonary Fibrosis. The Future of Quantitative Analysis. 2019; 199(1): 12-21.
6. Cottin V. Lung biopsy in interstitial lung disease: balancing the risk of surgery and diagnostic uncertainty. 2016; 48(5):1274-1277.

7. Shah R, Patel T, Freedman J E. Circulating Extracellular Vesicles in Human Disease. 2018; 379(10):958-966.

8. Hardie W D, Korfhagen T R, Sartor M A, et al. Genomic profile of matrix and vasculature remodeling in TGF-alpha induced pulmonary fibrosis. 2007; 37(3):309-321.

9. Hardie W D, Kerlakian C B, Bruno M D, et al. Reversal of lung lesions in transgenic transforming growth factor alpha mice by expression of mutant epidermal growth factor receptor. 1996; 15(4):499-508.

10. Nakashima N, Kuwano K, Maeyama T, et al. The p53-Mdm2 association in epithelial cells in idiopathic pulmonary fibrosis and non-specific interstitial pneumonia. 2005; 58(6):583-589.

11. Lagares D, Ghassemi-Kakroodi P, Tremblay C, et al. ADAM10-mediated ephrin-B2 shedding promotes myofibroblast activation and organ fibrosis. 2017; 23(12):1405-1415.

12. Kowdley K V, Belt P, Wilson L A, et al. Serum ferritin is an independent predictor of histologic severity and advanced fibrosis in patients with nonalcoholic fatty liver disease. 2012; 55(1):77-85.

13. Jung Y J, Katilius E, Ostroff R M, et al. Development of a Protein Biomarker Panel to Detect Non-Small-Cell Lung Cancer in Korea. 2017; 18(2):e99-e107.

14. Madala S K, Thomas G, Edukulla R, et al. p70 ribosomal S6 kinase regulates subpleural fibrosis following transforming growth factor-alpha expression in the lung. 2016; 310(2): L175-186.

15. Madala S K, Schmidt S, Davidson C, Ikegami M, Wert S, Hardie W D. MEK-ERK pathway modulation ameliorates pulmonary fibrosis associated with epidermal growth factor receptor activation. 2012; 46(3):380-388.

16. Madala S K, Korfhagen T R, Schmidt S, et al. Inhibition of the alphavbeta6 integrin leads to limited alteration of TGF-alpha-induced pulmonary fibrosis. 2014; 306(8): L726-735.

17. Madala S K, Edukulla R, Phatak M, et al. Dual targeting of MEK and PI3K pathways attenuates established and progressive pulmonary fibrosis. 2014; 9(1):e86536.

18. Le Cras T D, Korfhagen T R, Davidson C, et al. Inhibition of PI3K by PX-866 prevents transforming growth factor-alpha-induced pulmonary fibrosis. 2010; 176(2):679-686.

19. Korfhagen T R, Le Cras T D, Davidson C R, et al. Rapamycin prevents transforming growth factor-alpha induced pulmonary fibrosis. 2009; 41(5):562-572.

20. Hardie W D, Davidson C, Ikegami M, et al. EGF receptor tyrosine kinase inhibitors diminish transforming growth factor-alpha-induced pulmonary fibrosis. 2008; 294(6):L1217-1225.

21. Krefft S D, Rose C S, Nawaz S, Miller Y E. Deployment-Related Lung Disorders. 2015; 32(6):32-38.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. All accessioned information (e.g., as identified by PUBMED, PUBCHEM, NCBI, UNIPROT, or EBI accession numbers) and publications in their entireties are incorporated into this disclosure by reference in order to more fully describe the state of the art as known to those skilled therein as of the date of this disclosure. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A method for assessing stable versus progressive pulmonary fibrosis disease status in an individual in need thereof, comprising
   a. detecting a level of one or more biomarkers in a biomarker panel comprising Ephrin B2, Epidermal Growth Factor, Ferritin-heavy chain, Apotransferrin, Phosphoinositide 3-kinase, Mdm2-binding protein isoform X3, Tubulin polyglutamylase TTLL13 isoform X7, Heparin sulfate glucosamine 3-O-sulfotransferase 2, in a biological sample obtained from the individual;
   b. comparing the level of the one or more biomarkers to that of a control value;
   c. based on a comparison of the one or more biomarker level to a control value, characterizing the disease status in said individual as either progressive or stable; and
   d. where the disease status is determined to be progressive, administering a treatment to the individual selected from one or more of a PI3K pathway inhibitor, an EGF pathway inhibitor, Pirfenidone, and Nintendanib.

2. The method of claim 1, the biomarker panel further comprising a biomarker selected from pregnancy zone protein, serotransferrin, alpha-2-macroglobulin, immunoglobulin lambda-like polypeptide 5, ceruloplasmin, alpha-1-antitrypsin precursor, complement C3 preproprotein, coiled-coil domain-containing protein 144A, cytochrome P450 3A43, myosin phosphatase Rho-interacting protein, collagen alpha-6 (IV) chain protein FAM110A, DNA polymerase epsilon catalytic subunit A, semaphorin-5B ephrin type-B receptor 1, zinc finger protein 532, tyrosine—tRNA ligase (cytoplasmic), mismatch repair endonuclease PMS2, cadherin EGF LAG seven-pass G-type receptor, cytoskeleton-associated protein 2, tyrosine—tRNA ligase (cytoplasmic), zinc finger protein 618, cytoskeleton-associated protein 2, alpha-2-macroglobulin, serine/threonine-protein kinase OSR1, collagen alpha-1 (XII) chain, zinc finger ZZ-type and EF-hand domain-containing protein 1, iporin, phospholipid-transporting ATPase IG, collagen alpha-6 (IV) chain, spatacsin, short stature homeobox protein 2, collagen alpha-1 (XII) chain, ubiquitin carboxyl-terminal hydrolase 28, phospholipid-transporting ATPase IG, cyclin-dependent kinase 13, A-kinase anchor protein 9, zinc finger protein 417, sorting nexin-13, hemoglobin subunit beta, hemoglobin subunit delta, hemoglobin subunit alpha, cytochrome P450 3A4 isoform, filamin-C, apolipoprotein A-IV, nebulin, SAA2-SAA2 protein precursor, plasminogen isoform 1 precursor, ATPase family AAA domain-containing protein 5, DNA damage-induced apoptosis suppressor protein, E3 ubiquitin-protein ligase Midline-1, mitogen-activated protein kinase kinase kinase kinase 1, mucin-16, probable E3 ubiquitin-protein ligase HECTD4, protein RRP5 homolog, retrotransposon Gag-like protein 9, serine/threonine-protein phosphatase 2A regulatory subunit B" subunit gamma, and uncharacterized protein C12orf42.

3. The method of claim 1, further comprising identifying said individual as having improved disease, progressing disease, or a plateau in disease.

4. The method of claim 1, wherein an alteration in the biomarker level compared to the control level indicates the presence of disease or progression of disease.

5. The method of claim 1, wherein a second comparison step is carried out following administration of the treatment, wherein a return to the biomarker level to that of a control value indicates an improvement in disease.

6. The method of claim 1, wherein the pulmonary fibrosis disease is selected from progressive pulmonary fibrosis, interstitial lung disease (ILD), and idiopathic pulmonary fibrosis (IPF).

7. The method of claim 1, wherein the treatment is selected from erlotinib, cetuximab, panitumumab, lapatinib, and canertinib.

8. The method of claim 1, wherein the individual has one or more predispositions selected from a familial history of IPF, age of 60 years or greater, and a history of chronic smoking.

9. A method of diagnosing and treating a pulmonary disease in an individual in need thereof, comprising
    a) establishing, using a computing system, a model for characterizing a disease state of an individual having or likely to have a pulmonary disease, by using expression level data of a biomarker panel comprising Ephrin B2, Epidermal Growth Factor, Ferritin-heavy chain, Apo-transferrin, Phosphoinositide 3-kinase, Mdm2-binding protein isoform X3, Tubulin polyglutamylase TTLL13 isoform X7, and Heparin sulfate glucosamine 3-O-sulfotransferase 2;
    b) contacting a biological sample from said individual with at least one detection agent capable of specifically binding to one or more biomarkers of the biomarker panel;
    c) acquiring an expression level from the one or more biomarkers measured from said biological sample;
    d) characterizing the individual as one or more of likely to have a lung disease, having stable lung disease, having progressive lung disease, or having improving lung disease; and
    e) administering a therapy to said individual based on the characterization, wherein the therapy is selected from one or more of a PI3K pathway inhibitor, an EGF pathway inhibitor, Pirfenidone, and Nintendanib.

10. The method of claim 9, wherein said disease is idiopathic pulmonary fibrosis (IPF).

11. The method of claim 1, wherein the biological sample is a plasma sample.

12. The method of claim 9, wherein the biological sample is a plasma sample.

13. The method of claim 1, wherein each of the one or more biomarkers is a protein biomarker.

14. The method of claim 9, wherein each of the one or more biomarkers is a protein biomarker.

\* \* \* \* \*